(12) United States Patent
Ratkaj et al.

(10) Patent No.: US 8,501,960 B2
(45) Date of Patent: Aug. 6, 2013

(54) SAXAGLIPTIN INTERMEDIATES, SAXAGLIPTIN POLYMORPHS, AND PROCESSES FOR PREPARATION THEREOF

(75) Inventors: Marina Ratkaj, Zagreb (HR); Tomislav Biljan, Krizevci (HR); Marina Marinkovic, Sesvete-Zagreb (HR)

(73) Assignee: Assia Chemical Industries Ltd., Petach Tikva (IL)

( * ) Notice: Subject to any disclaimer, the term of this patent is extended or adjusted under 35 U.S.C. 154(b) by 242 days.

(21) Appl. No.: 13/101,491

(22) Filed: May 5, 2011

(65) Prior Publication Data

US 2011/0275687 A1 Nov. 10, 2011

Related U.S. Application Data

(60) Provisional application No. 61/331,526, filed on May 5, 2010, provisional application No. 61/345,200, filed on May 17, 2010, provisional application No. 61/452,504, filed on Mar. 14, 2011.

(51) Int. Cl.
*C07D 209/52* (2006.01)
*A61K 31/403* (2006.01)

(52) U.S. Cl.
USPC .......................................... 548/452; 514/412

(58) Field of Classification Search
None
See application file for complete search history.

(56) References Cited

U.S. PATENT DOCUMENTS

| 6,395,767 | B2 | 5/2002 | Robl et al. |
|---|---|---|---|
| 6,995,183 | B2 | 2/2006 | Hamann et al. |
| 7,186,846 | B2 | 3/2007 | Sharma et al. |
| 7,214,702 | B2 | 5/2007 | Sharma |
| 7,223,573 | B2 | 5/2007 | Patel et al. |
| 7,420,079 | B2 | 9/2008 | Vu et al. |
| 7,470,810 | B2 | 12/2008 | Sharma et al. |
| 7,741,082 | B2 | 6/2010 | Politino et al. |
| 2006/0035954 | A1 | 2/2006 | Sharma et al. |
| 2009/0054303 | A1 | 2/2009 | Gougoutas et al. |

FOREIGN PATENT DOCUMENTS

| WO | WO-01/68603 | 9/2001 |
|---|---|---|
| WO | WO-2005/117841 | 12/2005 |
| WO | WO-2008/131149 | 10/2008 |

OTHER PUBLICATIONS

Savage, Scott A., et al., "Preparation of Saxagliptin, a Novel DPP-IV Inhibitor", Organic Process Research & Development, 2009, vol. 13, pp. 1169-1176.
Advanced Synthesis & Catalysis (2007), 349 (8+9), 1369-1378; Author(s): Ronald L. Hanson, et al., Bristol-Meyers Squibb Company.
Bioorganic Medicinal Chemistry Letters (2006), 16(3), 705-709; Author(s): Iqbal Gill, et al., Bristol-Meyers Squibb Company.
Bioorganic & Medicinal Chemistry Letters (1998), 8, 2123-2128, Author(s): Stephen Hanessian et al., Dept. Chemistry, Université de Montréal.
Journal of Medicinal Chemistry (2005), 48, 5025-5037, Authors: David J. Augeri et al., Bristol-Meyers Squibb Company.
Drugs of the Future (2008), 33(7), 577-586, Authors: P. Cole, J. Bolós, R. Castañer, Bristol-Meyers Squibb Company.
Enzyme and Microbial Technology (2011), 48, 445-453, Authors: R. L. Hanson, R. M. Johnston, S.L. Goldberg, W. L. Parker, R. N. Patel, Bristol-Meyers Squibb Company.

*Primary Examiner* — Nyeemah A Grazier
(74) *Attorney, Agent, or Firm* — Kenyon & Kenyon LLP

(57) ABSTRACT

The invention provides Saxagliptin Schiff bases, polymorphs of Saxagliptin and (1S,3S,5S)-2-[(2S)-2-propan-2-ylidene-amino-2-(3-hydroxy-1-adamantyl)acetyl]-2-azabicyclo[3.1.0]hexane-3-carbonitrile, processes for preparing Saxagliptin hydrates, and pharmaceutical compositions thereof.

24 Claims, 13 Drawing Sheets

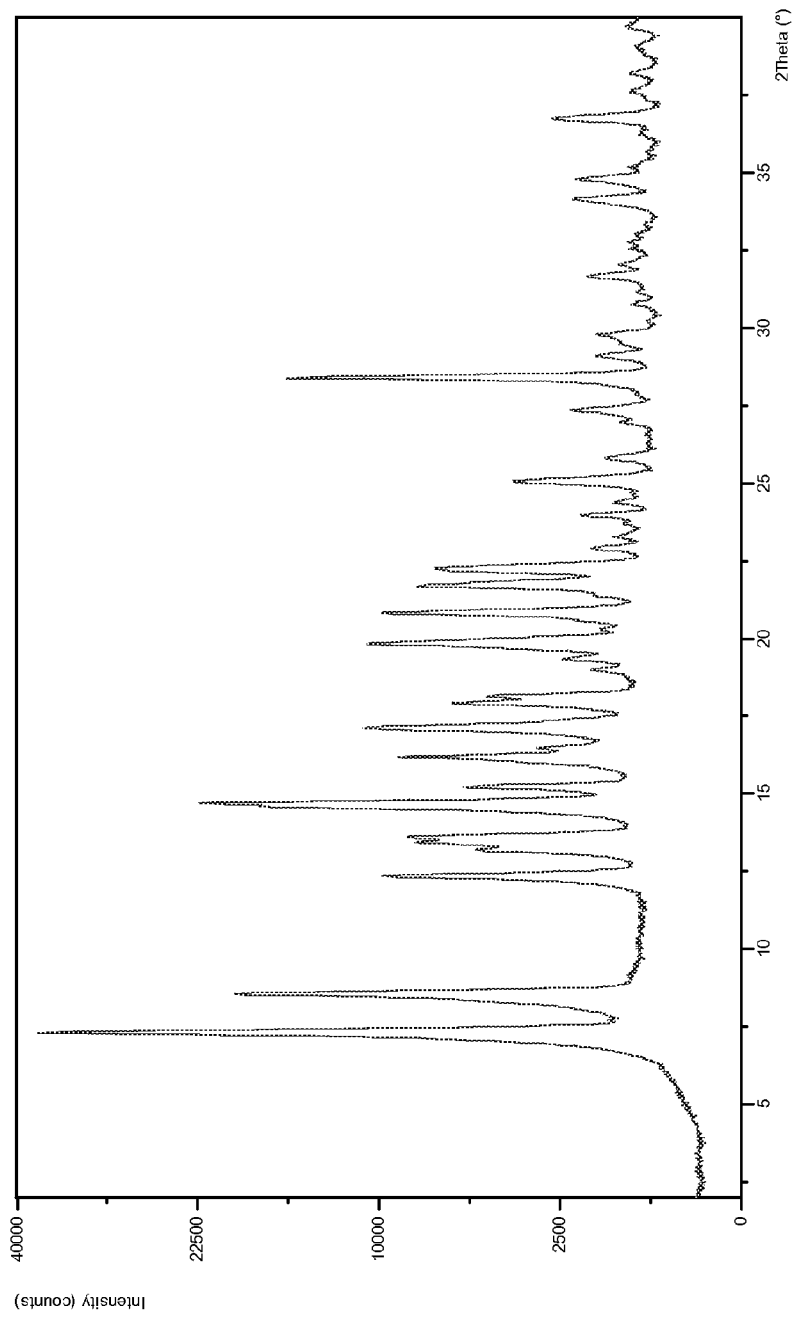
Figure 1 shows a powder XRD pattern of crystalline Saxagliptin designated form F1, in a mixture with crystalline Saxagliptin monohydrate H-1. Peak at 28.37 belongs to silicon.

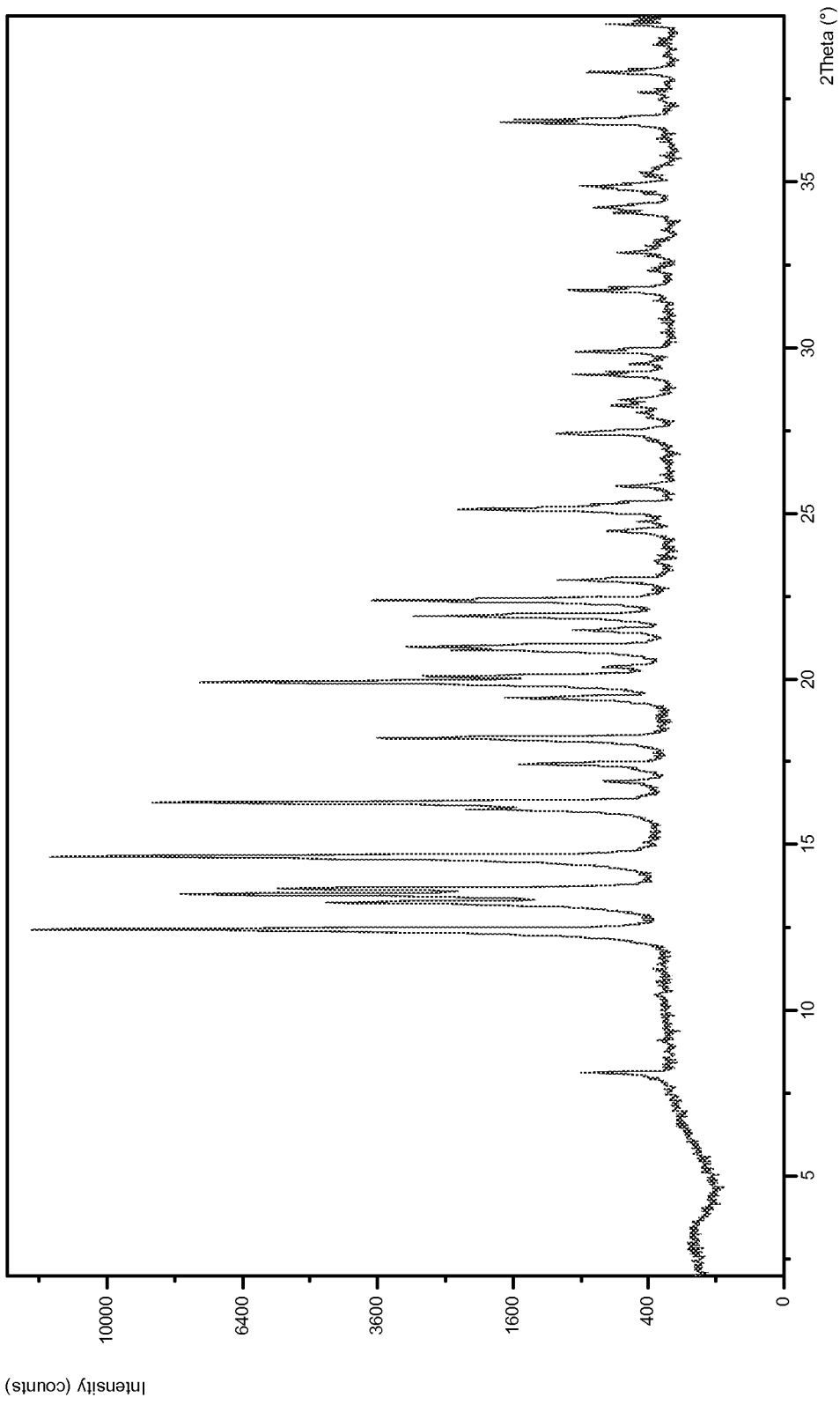
Figure 2 shows a powder XRD pattern of crystalline Saxagliptin monohydrate form H-1.

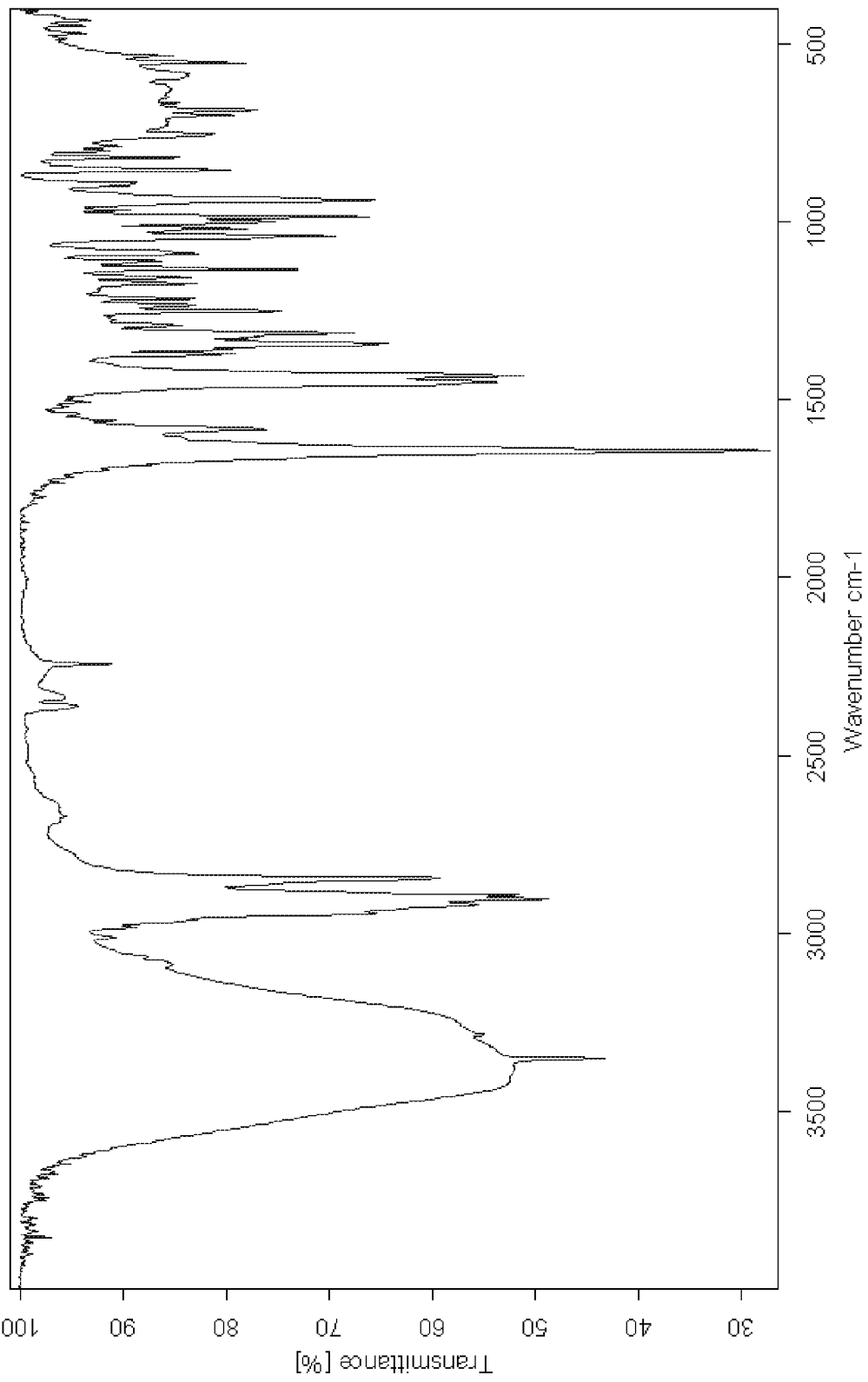
Figure 3 shows a FT-IR pattern of crystalline Saxagliptin monohydrate form H-1.

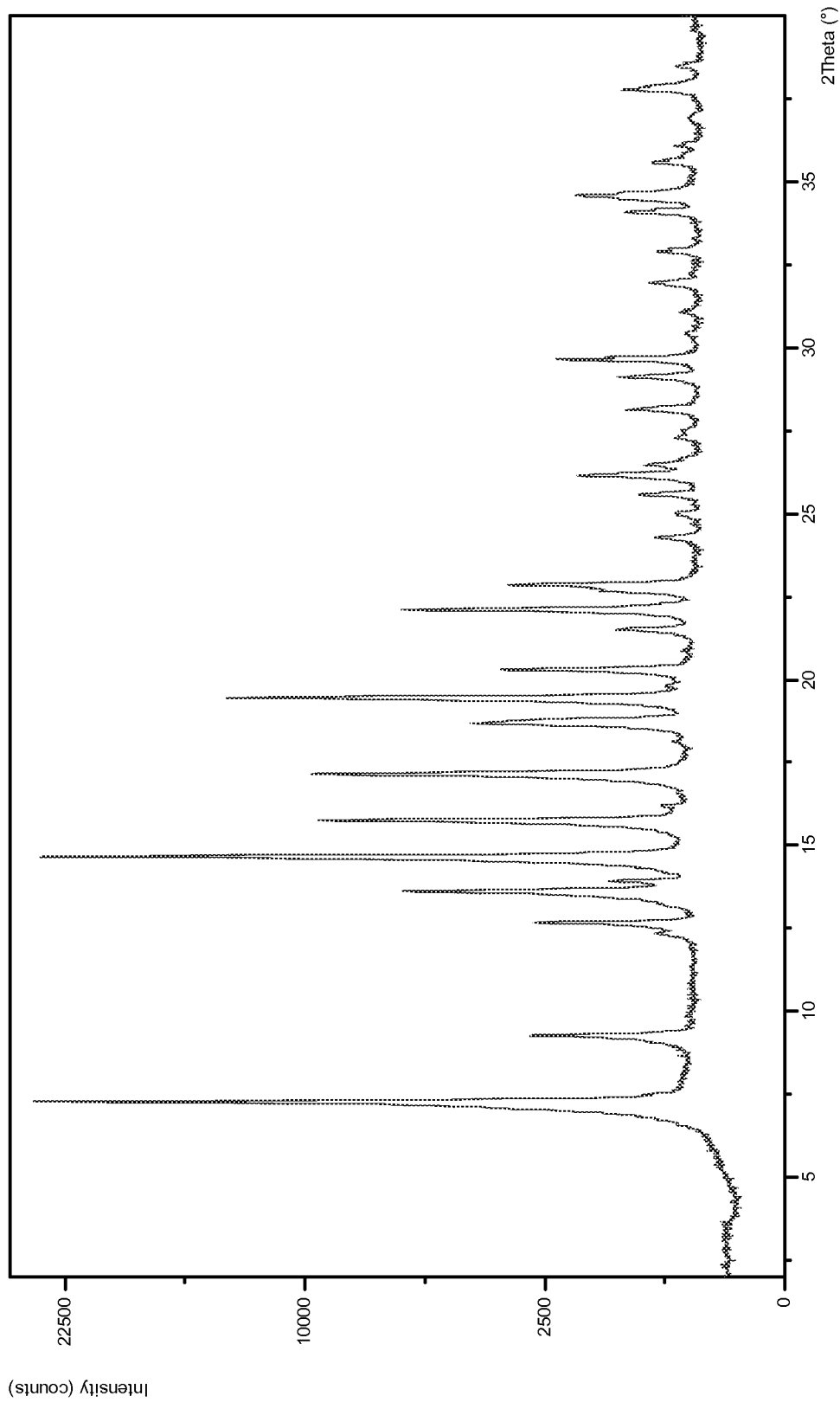

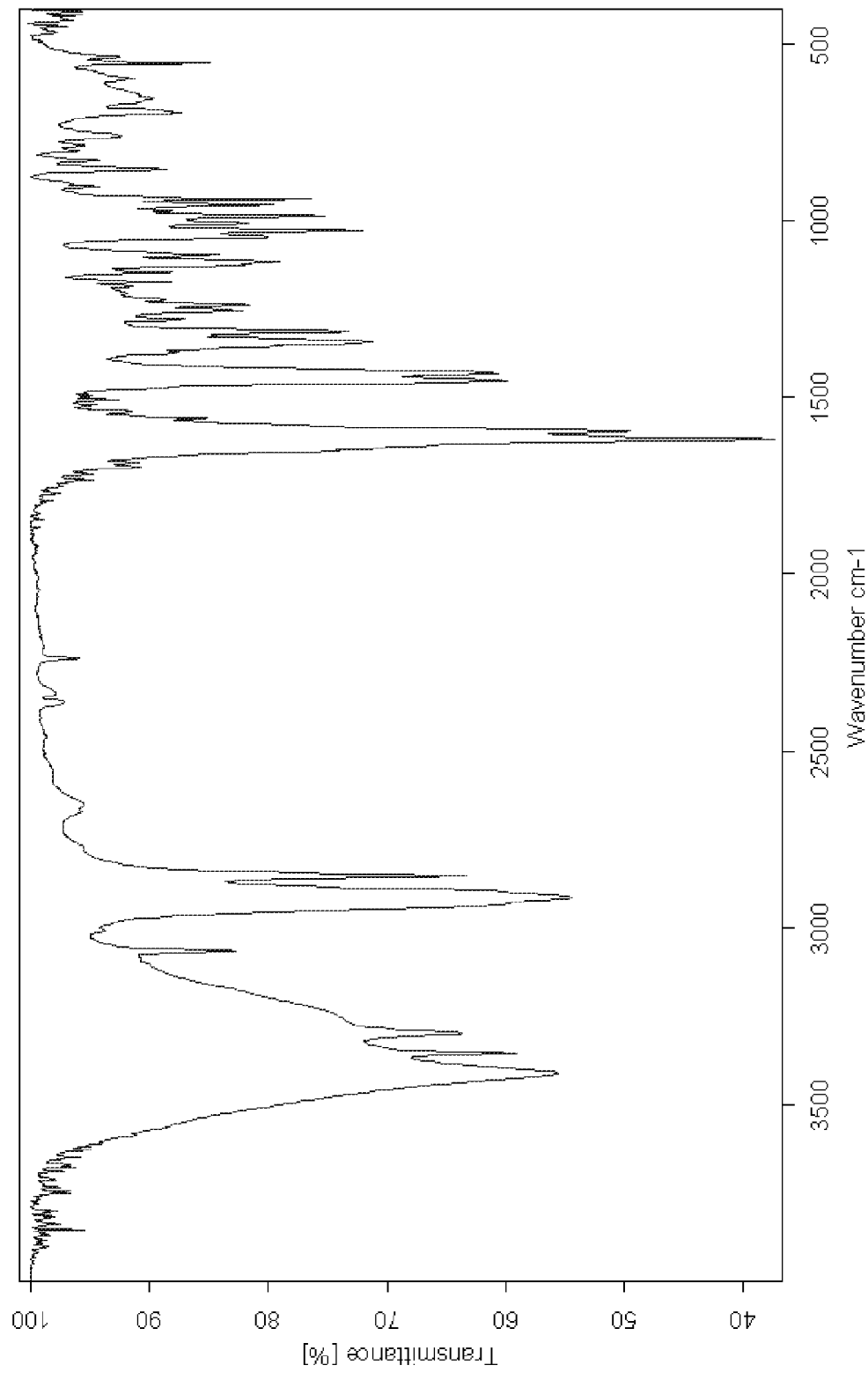
Figure 5 shows a FT-IR pattern of crystalline Saxagliptin hemihydrate form H0.5-2.

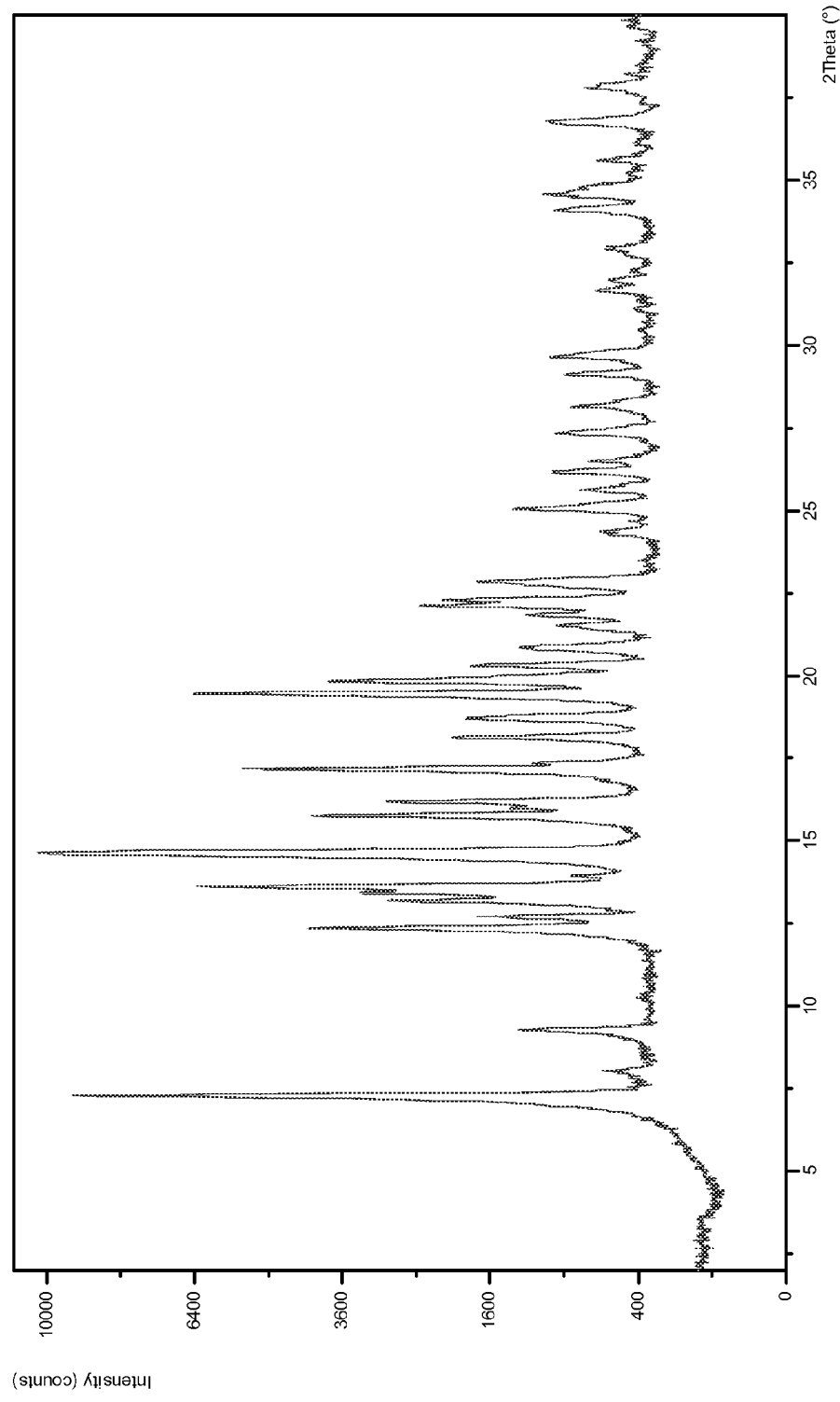
Figure 6 shows a powder XRD pattern of a mixture of crystalline Saxagliptin monohydrate form H-1 and crystalline Saxagliptin hemihydrate form H0.5-2

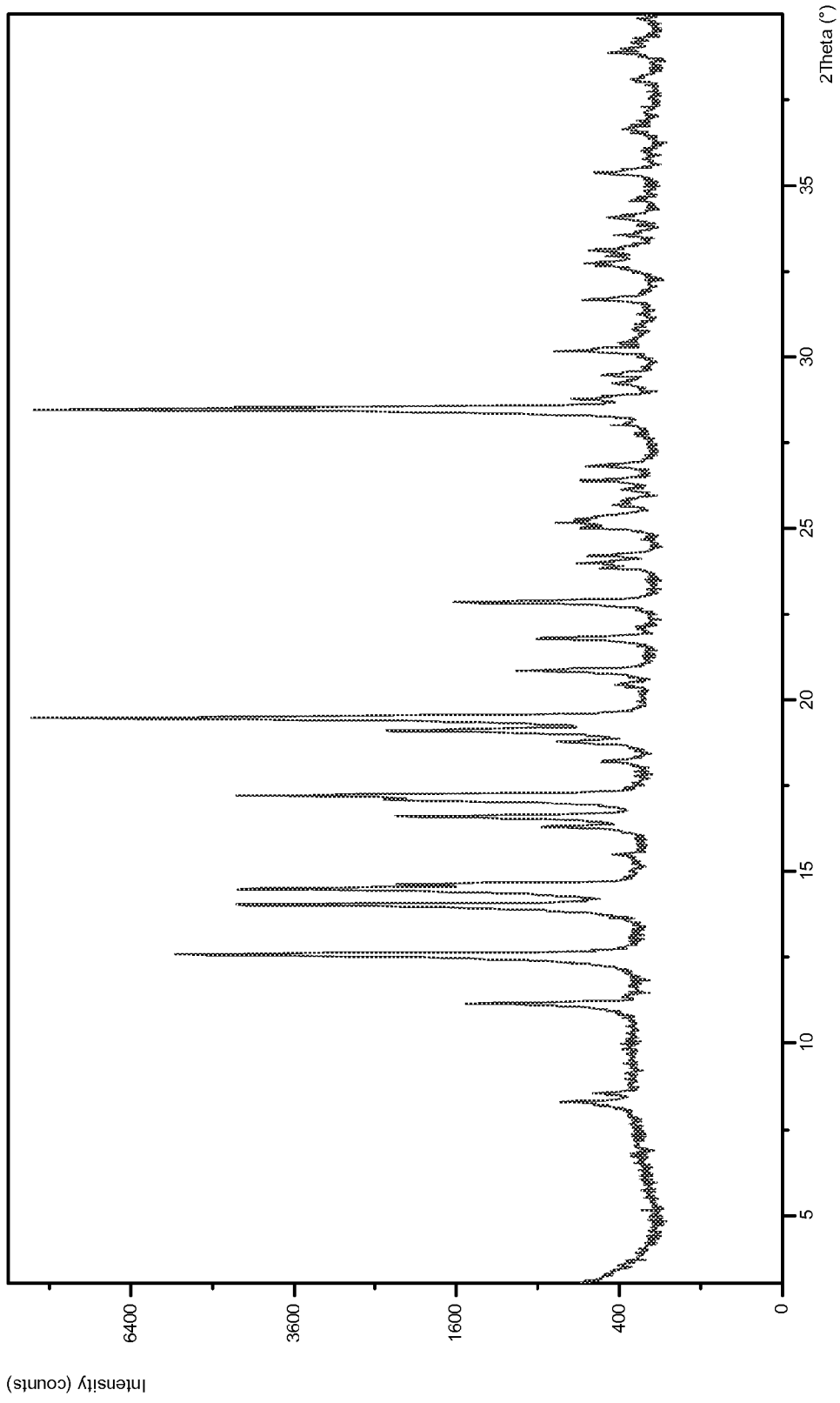
Figure 7 shows a powder XRD pattern of crystalline compound M. Peak at 28.46 belongs to silicon.

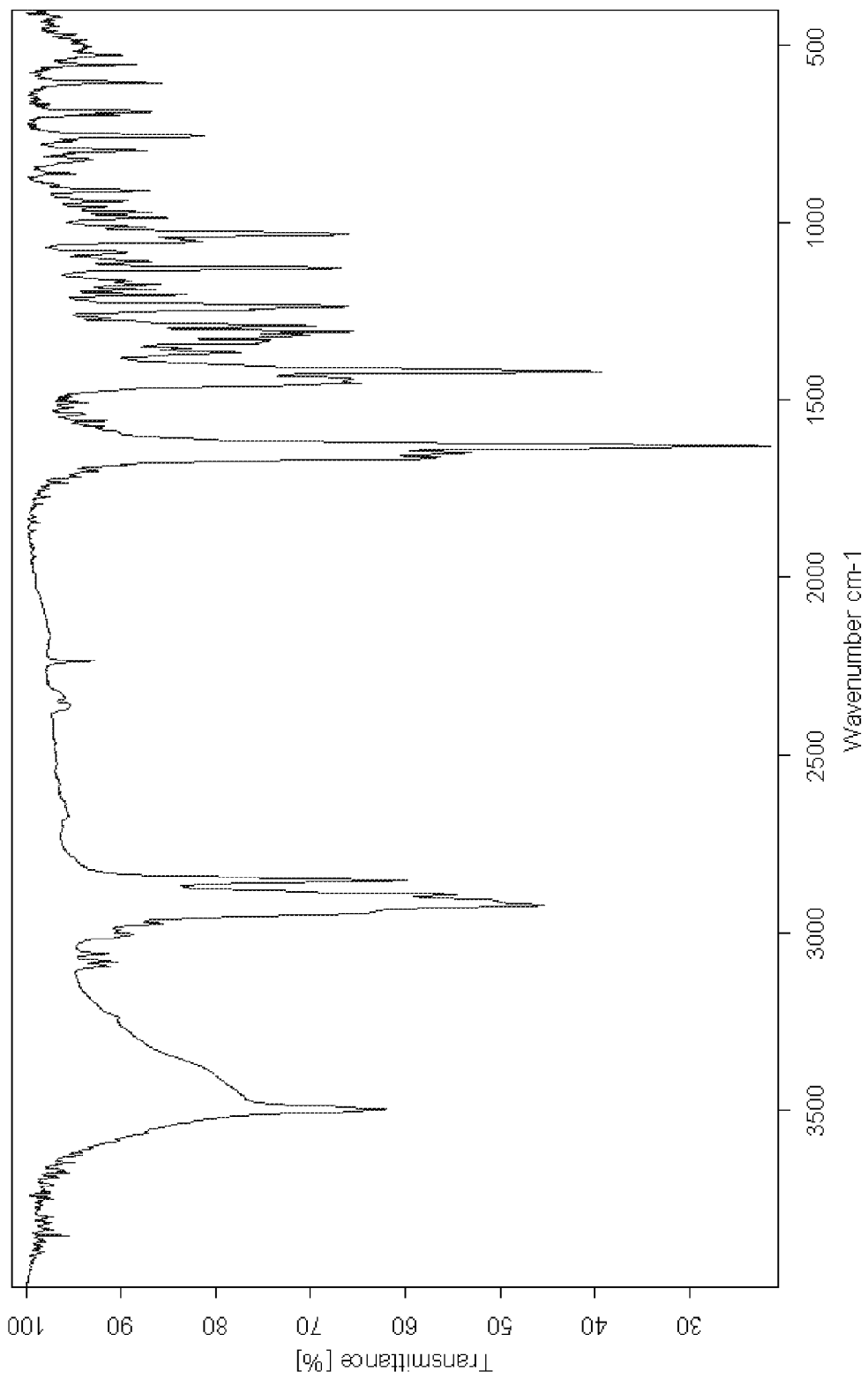
Figure 8 shows a FT-IR spectrum of crystalline compound M.

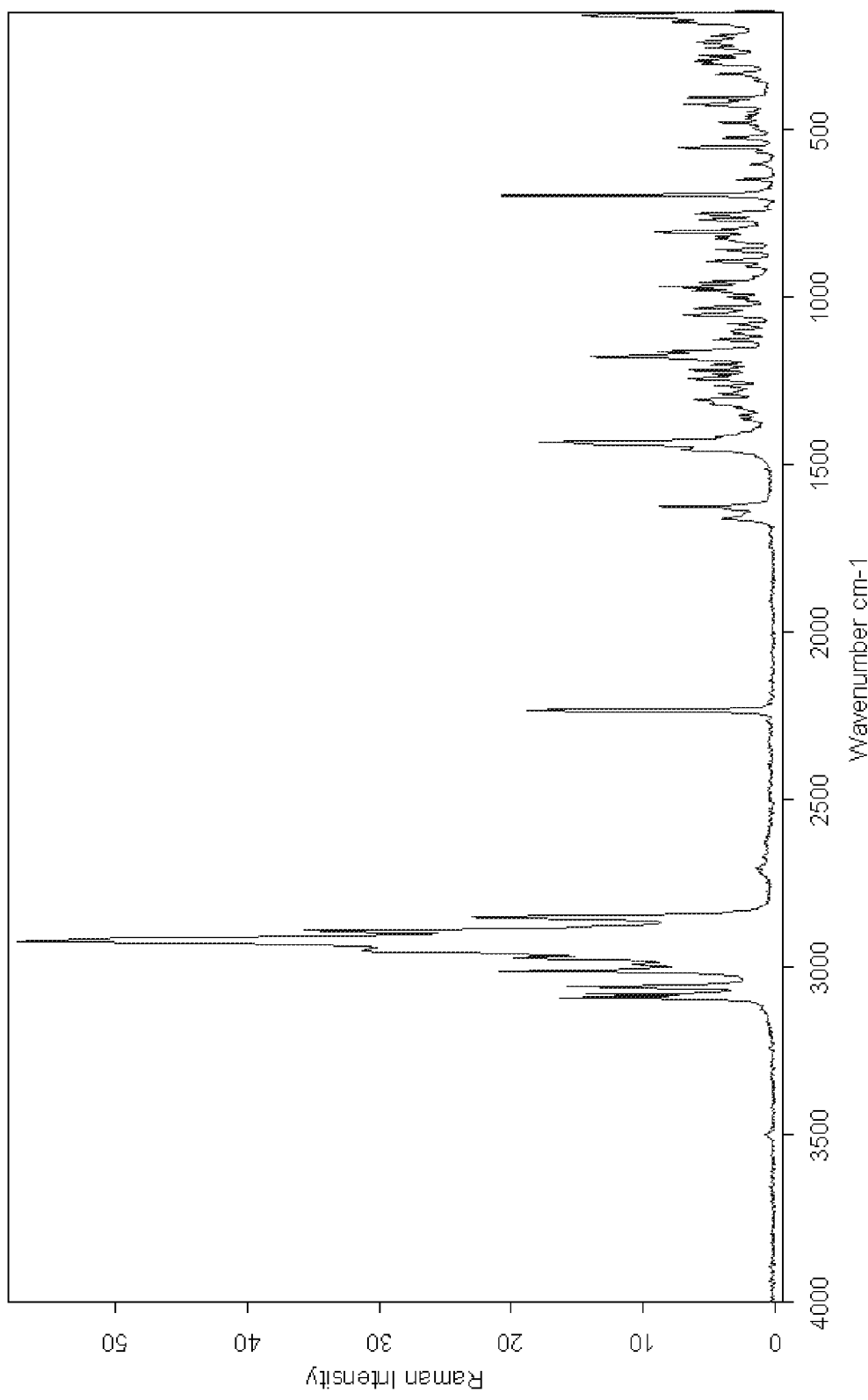
Figure 9 shows a FT-IR Raman spectrum of crystalline compound M

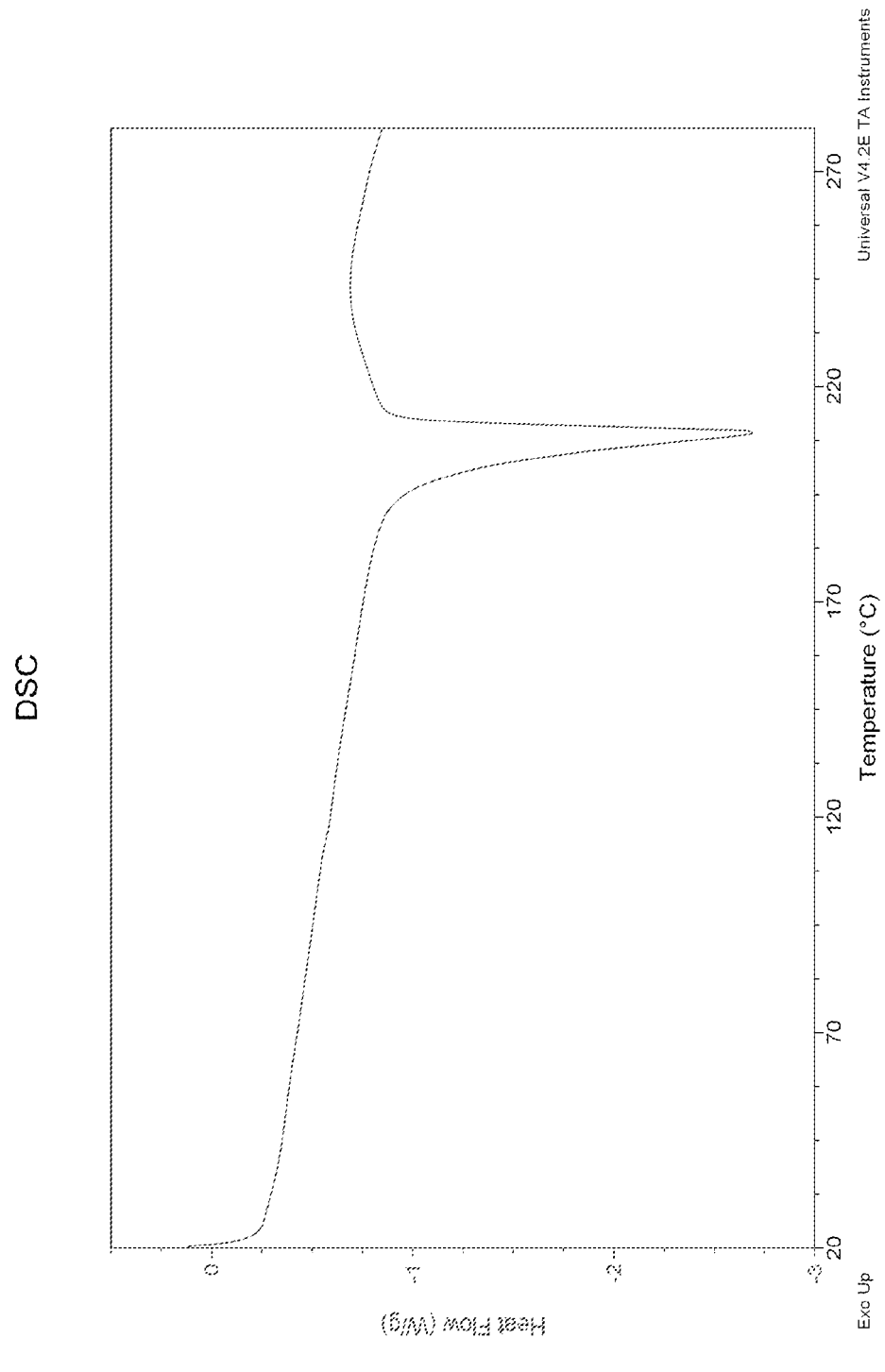
Figure 10 shows a DSC thermogram of crystalline compound M

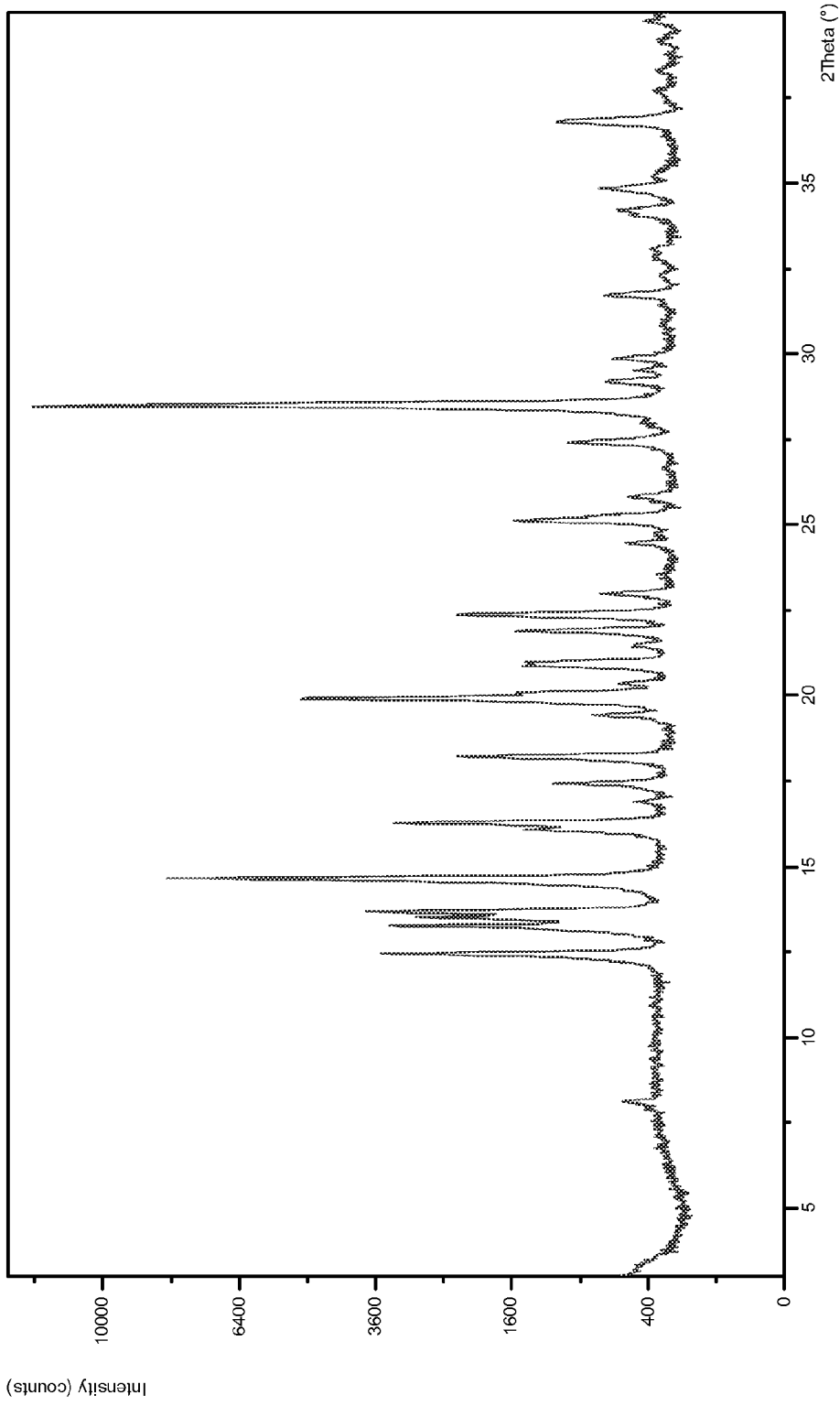
Figure 11 shows a powder XRD pattern of crystalline Saxagliptin monohydrate form H-1 prepared according to example 17. Peak at 28.47 belongs to silicon.

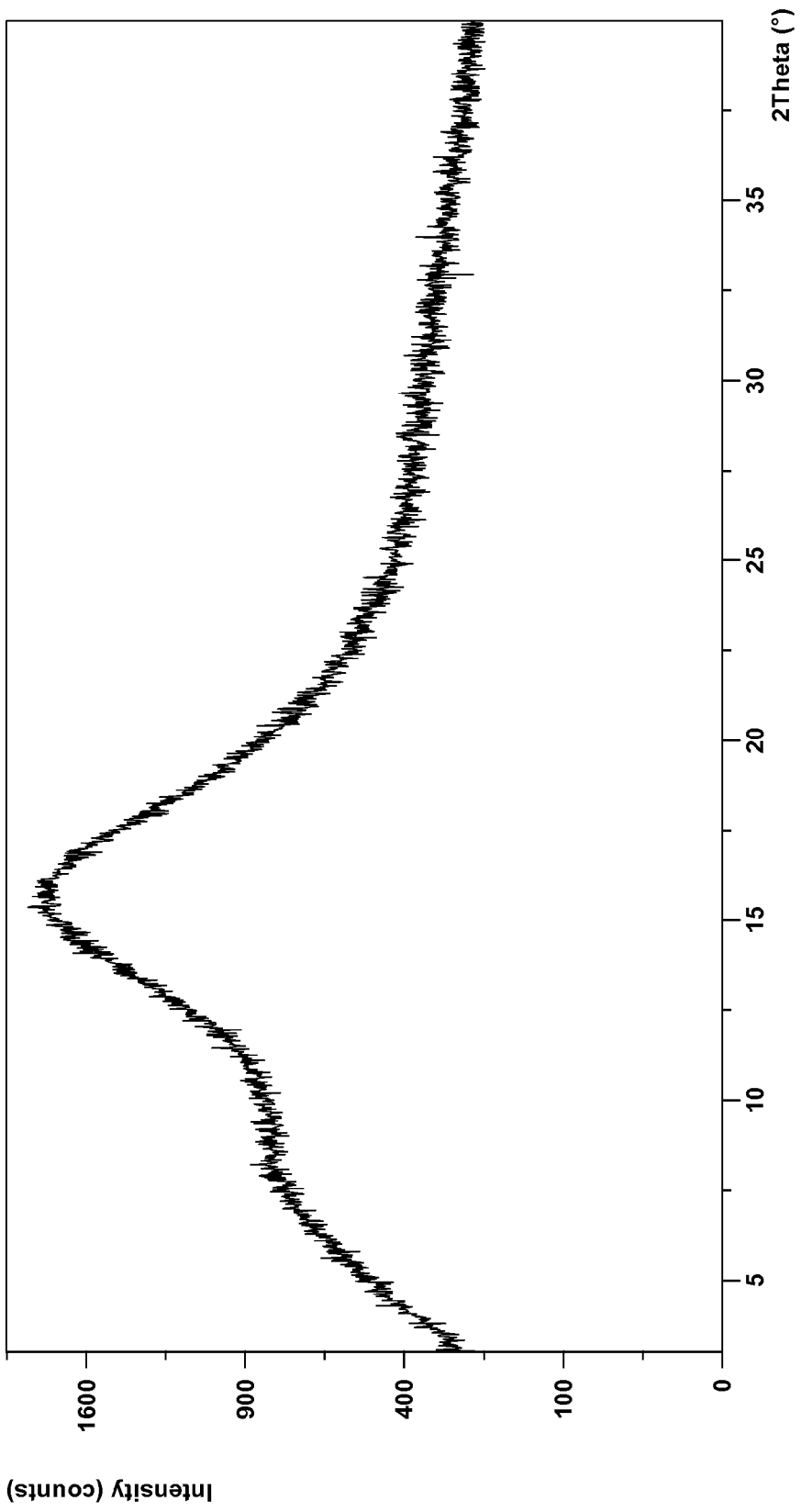
Figure 12 shows a powder XRD pattern of amorphous Saxagliptin

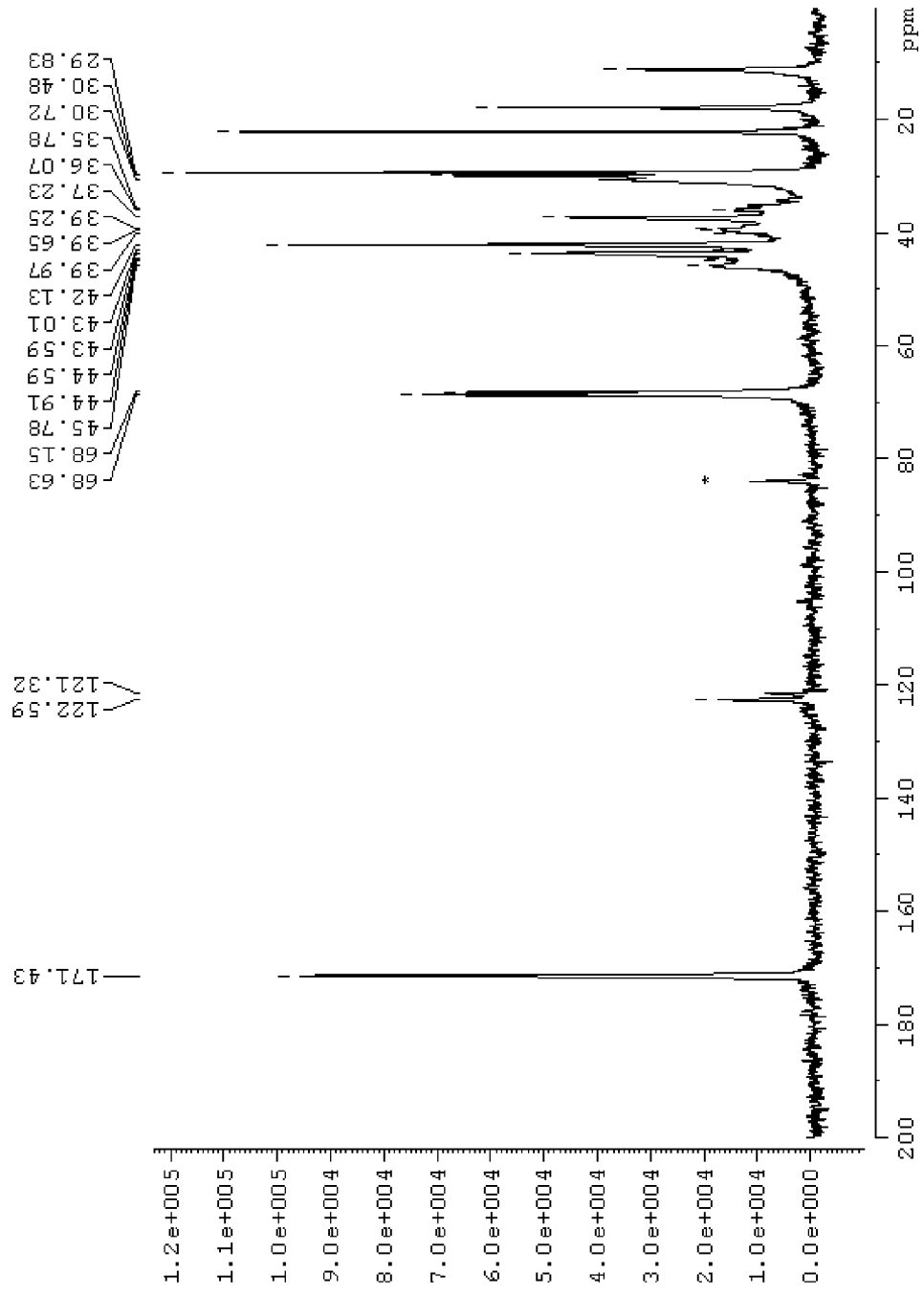
Figure 13 shows a solid state NMR of crystalline compound M

SAXAGLIPTIN INTERMEDIATES, SAXAGLIPTIN POLYMORPHS, AND PROCESSES FOR PREPARATION THEREOF

RELATED APPLICATIONS

This application claims the benefit under 35 U.S.C. §119 (e) of U.S. Provisional Application Nos. 61/331,526 filed May 5, 2010; 61/345,200 filed May 17, 2010; 61/452,504 filed Mar. 14, 2011, each of which is incorporated herein by reference in its entirety

FIELD OF THE INVENTION

The invention relates to Saxagliptin Schiff bases, polymorphs of Saxagliptin and (1S,3S,5S)-2-[(2S)-2-propan-2-ylideneamino-2-(3-hydroxy-1-adamantyl)acetyl]-2-azabicyclo[3.1.0]hexane-3-carbonitrile, processes for preparing Saxagliptin hydrates, and pharmaceutical compositions thereof.

BACKGROUND OF THE INVENTION

Saxagliptin, (1S,3S,5S)-2-((2S)-2-Amino-2-(3-hydroxy-adamantan-1-yl)-acetyl)-2-azabicyclo[3.1.0]hexane-3-carbonitrile of the following chemical structure:

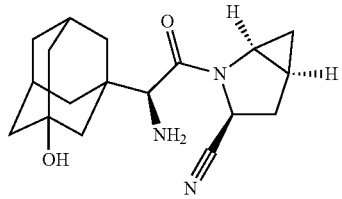 [SMILES: N#C[C@@H]1C[C@@H]2C[C@@H]2N1C(=O)[C@@H](N)C12CC3CC(CC(O)(C3)C1)C2]

is reported to be a dipeptidyl peptidase IV (DPP4) inhibitor. Saxagliptin is marketed under the trade name ONGLYZA® by Bristol-Myers Squibb for the treatment of type 2 diabetes.

Saxagliptin, and its hydrochloride and trifluoroacetic acid salts are disclosed in U.S. Pat. Nos. 6,395,767, and 7,420,079 discloses Saxagliptin and its hydrochloride, trifluoroacetic acid and benzoate salts, as well as Saxagliptin monohydrate.

U.S. 2009/054303 and the corresponding WO 2008/131149 disclose several crystalline forms of Saxagliptin and of Saxagliptin salts. The crystalline forms of Saxagliptin reported in this patent application are a monohydrate (denoted there as form H-1), a hemihydrate (denoted there as form H0.5-2), and an anhydrous form (denoted there as N-3).

WO 2005/117841 (the '841 application) describes the cyclization of Saxagliptin to form the therapeutically inactive cyclic amidine. The '841 application reports that this cyclization can occur both in solid state and solution state.

Polymorphism, the occurrence of different crystal forms, is a property of some molecules and molecular complexes. A single molecule, like Saxagliptin, may give rise to a variety of polymorphic forms having distinct crystal structures and physical properties like melting point, X-ray diffraction (XRD) pattern, infrared absorption fingerprint, and solid state NMR spectrum. One polymorphic form may give rise to thermal behavior different from that of another polymorphic form. Thermal behavior can be measured in the laboratory by such techniques as capillary melting point, thermogravimetric analysis (TGA), and differential scanning calorimetry (DSC) as well as content of solvent in the polymorphic form, which have been used to distinguish polymorphic forms.

The difference in the physical properties of different polymorphic forms results from the orientation and intermolecular interactions of adjacent molecules or complexes in the bulk solid. Accordingly, polymorphs are distinct solids sharing the same molecular formula yet having distinct advantageous physical properties compared to other polymorphic forms of the same compound or complex.

One of the most important physical properties of pharmaceutical compounds is their solubility in aqueous solution, particularly their solubility in the gastric juices of a patient. For example, where absorption through the gastrointestinal tract is slow, it is often desirable for a drug that is unstable to conditions in the patient's stomach or intestine to dissolve slowly so that it does not accumulate in a deleterious environment. Different polymorphic forms or polymorphs of the same pharmaceutical compounds can and reportedly do have different aqueous solubilities.

The discovery of new polymorphic forms of Saxagliptin and Saxagliptin intermediates provides new opportunities to improve the synthesis and the characteristics of the active pharmaceutical ingredient (API). It enlarges the repertoire of materials that a formulation scientist has available for designing, for example, a pharmaceutical dosage form of a drug with a targeted release profile or other desired characteristic.

Therefore, there is a need for additional solid state forms of Saxagliptin and Saxagliptin intermediates, and additional methods for preparing Saxagliptin crystal forms that provide Saxagliptin efficiently, and can be applied in an industrial scale.

SUMMARY OF THE INVENTION

In one embodiment the invention encompasses Saxagliptin Schiff bases.

In another embodiment the invention encompasses Saxagliptin Schiff bases of Formula I (wherein the stereochemistry is not defined):

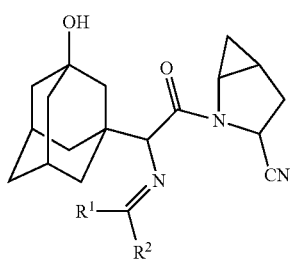

Formula I wherein $R^1$ is —H or $C_{1-4}$ alkyl and $R^2$ is H or $C_{1-4}$ alkyl, phenyl or substituted phenyl, wherein phenyl may be substituted with, for example, $C_{1-4}$ alkyl, halogen, or $C_{1-4}$ alkoxy.

In yet another embodiment the invention encompasses Saxagliptin Schiff bases of Formula I (wherein the stereochemistry is not defined):

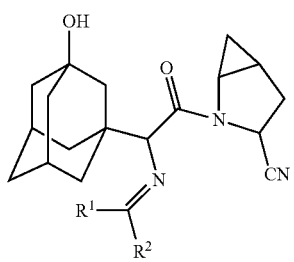

Formula I wherein R¹ is —H or $C_{1-4}$ alkyl and R² is $C_{1-4}$ alkyl, phenyl or substituted phenyl, wherein phenyl may be substituted with, for example, $C_{1-4}$ alkyl, halogen, or $C_{1-4}$ alkoxy.

In another embodiment, the present invention encompasses Saxagliptin Schiff bases having fixed stereochemistry according to the following formula Ia:

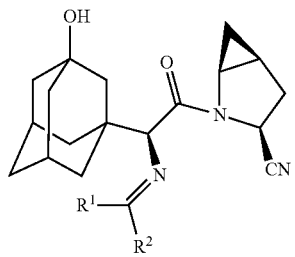

Formula Ia wherein R¹ is —H or $C_{1-4}$ alkyl and R² is H or $C_{1-4}$ alkyl, phenyl or substituted phenyl, wherein phenyl may be substituted with, for example, $C_{1-4}$ alkyl, halogen (particularly Cl, Br or I, more preferably Cl or Br), or $C_{1-4}$ alkoxy. Preferably the substituents on the phenyl are $C_{1-4}$ alkyl or $C_{1-4}$ alkoxy. Preferably, R¹ is $C_{1-4}$ alkyl. R² is preferably $C_{1-4}$ alkyl or unsubstituted phenyl. More preferably, R¹ and R² are each independently selected from $C_{1-4}$ alkyl. In preferred embodiments, R¹ and R² are the same, and are preferably selected from $C_{1-4}$ alkyl, particularly $C_{1-3}$ alkyl and particularly methyl or ethyl. Preferably, R¹ and R² are methyl.

In yet another embodiment, the present invention encompasses Saxagliptin Schiff bases having fixed stereochemistry according to the following formula Ia:

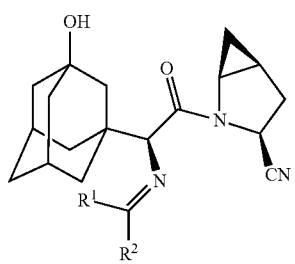

Formula Ia wherein R¹ is —H or $C_{1-4}$ alkyl and R² is $C_{1-4}$ alkyl, phenyl or substituted phenyl, wherein phenyl may be substituted with, for example, $C_{1-4}$ alkyl, halogen (particularly Cl, Br or I, more preferably Cl or Br), or $C_{1-4}$ alkoxy. Preferably the substituents on the phenyl are $C_{1-4}$ alkyl or $C_{1-4}$ alkoxy. Preferably, R¹ is $C_{1-4}$ alkyl. R² is preferably $C_{1-4}$ alkyl or unsubstituted phenyl. More preferably, R¹ and R² are each independently selected from $C_{1-4}$ alkyl. In preferred embodiments, R¹ and R² are the same, and are preferably selected from $C_{1-4}$ alkyl, particularly $C_{1-3}$ alkyl and particularly methyl or ethyl. Preferably, R¹ and R² are methyl.

In another embodiment the invention encompasses (1S,3S,5S)-2-[(2S)-2-propan-2-ylideneamino-2-(3-hydroxy-1-adamantyl)acetyl]-2-azabicyclo[3.1.0]-hexane-3-carbonitrile, referred to herein as Compound M:

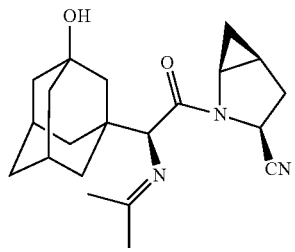

Compound M

In yet another embodiment the invention encompasses crystalline compound M. Crystalline compound M can be characterized by data selected from: a powder XRD pattern with peaks at 11.2, 12.6, 14.0, 16.6, and 19.5±0.2 degrees 2-theta, a powder X-ray diffraction (XRD) pattern substantially as depicted in FIG. 7, and combinations thereof.

In another embodiment the invention encompasses Schiff bases of Saxagliptin, in particular the above described compounds according to formulae I and Ia, and the compound M, for use in preparation of pharmaceutical formulation.

In another embodiment the invention encompasses Schiff bases of Saxagliptin, in particular the above described compounds according to formulae I and Ia, and the compound M, for use in preparation of (a) Saxagliptin and polymorphs thereof; (b) Saxagliptin salts, preferably Saxagliptin hydrochloride and polymorphs thereof; and (c) formulations of Saxagliptin or Saxagliptin salts, preferably Saxagliptin hydrochloride.

In yet another embodiment the invention encompasses a process for preparing Saxagliptin, Saxagliptin salts and polymorphic forms thereof; comprising preparing Schiff bases of Saxagliptin, in particular the above described compounds according to formulae I and Ia, and the compound M by the process of the present invention and converting them to Saxagliptin, Saxagliptin salts and polymorphs thereof.

In one embodiment the invention encompasses crystalline Saxagliptin, designated form FI, characterized by a powder XRD pattern having peaks at 7.4, 8.6, 15.3, 17.1, and 18.0±0.2 degrees 2-Theta.

In yet another embodiment, the invention encompasses the above described polymorph of Saxagliptin for use for the manufacture of a medicament for the treatment of type 2 diabetes.

In yet another embodiment, the invention encompasses a pharmaceutical composition comprising the above described polymorph of Saxagliptin and at least one pharmaceutically acceptable excipient.

In one embodiment the invention encompasses a process for preparing crystalline Saxagliptin monohydrate form H-1, as described below.

In another embodiment the invention encompasses a process for preparing crystalline Saxagliptin hemihydrate form H0.5-2, as described below.

In yet another embodiment the invention encompasses a process for preparing a mixture of crystalline Saxagliptin monohydrate form H-1 and crystalline Saxagliptin hemihydrate form H0.5-2, as described below.

BRIEF DESCRIPTION OF THE FIGURES

FIG. 1 shows a powder X-ray diffraction (XRD) pattern of crystalline Saxagliptin designated form FI, in a mixture with crystalline Saxagliptin monohydrate H-1.

FIG. 2 shows a powder XRD pattern of crystalline Saxagliptin monohydrate form H-1.

FIG. 3 shows a Fourier Transform Infrared (FT-IR) spectrum of crystalline Saxagliptin monohydrate form H-1.

FIG. 4 shows a powder XRD pattern of crystalline Saxagliptin hemihydrate form H0.5-2.

FIG. 5 shows a FT-IR spectrum of crystalline Saxagliptin hemihydrate form H0.5-2

FIG. 6 shows a powder XRD pattern of a mixture of crystalline Saxagliptin monohydrate form H-1 and crystalline Saxagliptin hemihydrate form H0.5-2.

FIG. 7 shows a powder XRD pattern of crystalline (1S,3S,5S)-2-[(2S)-2-propan-2-ylideneamino-2-(3-hydroxy-1-adamantyl)acetyl]-2-azabicyclo[3.1.0]-hexane-3-carbonitrile (crystalline compound M).

FIG. 8 shows a FT-IR spectrum of crystalline (1S,3S,5S)-2-[(2S)-2-propan-2-ylideneamino-2-(3-hydroxy-1-adamantyl)acetyl]-2-azabicyclo[3.1.0]hexane-3-carbonitrile (crystalline compound M).

FIG. 9 shows a Fourier transform (FT) Raman spectrum of crystalline (1S,3S,5S)-2-[(2S)-2-propan-2-ylideneamino-2-(3-hydroxy-1-adamantyl)acetyl]-2-azabicyclo[3.1.0]hexane-3-carbonitrile (crystalline compound M).

FIG. 10 shows a differential scanning calorimetry (DSC) thermogram of crystalline (1S,3S,5S)-2-[(2S)-2-propan-2-ylideneamino-2-(3-hydroxy-1-adamantyl)-acetyl]-2-azabicyclo[3.1.0]hexane-3-carbonitrile (crystalline compound M).

FIG. 11 shows a powder XRD pattern of crystalline Saxagliptin monohydrate form H-1 prepared according to example 17.

FIG. 12 shows a powder XRD pattern of amorphous Saxagliptin.

FIG. 13 shows solid state Nuclear magnetic resonance (NMR) spectrum of crystalline (1S,3S,5S)-2-[(2S)-2-propan-2-ylideneamino-2-(3-hydroxy-1-adamantyl)-acetyl]-2-azabicyclo[3.1.0]hexane-3-carbonitrile (crystalline compound M).

DETAILED DESCRIPTION OF THE INVENTION

The invention relates to Schiff bases of (1S,3S,5S)-2-((2S)-2-amino-2-(3-hydroxyadamantan-1-yl)acetyl)-2-azabicyclo[3.1.0]hexane-3-carbonitrile, Saxagliptin. Saxagliptin Schiff bases of the present invention, in particular compound M, can be used as novel intermediates in the preparation of Saxagliptin and polymorphs thereof, in particular Saxagliptin hydrates (e.g. Saxagliptin forms H-1 and H0.5-2, particularly form H-1) and Saxagliptin salts and polymorphs thereof (in particular Saxagliptin hydrochloride). The invention also provides a novel crystalline form of Saxagliptin, as well as processes for preparing Saxagliptin hydrates, and pharmaceutical compositions containing these forms of Saxagliptin.

The novel Saxagliptin Schiff bases intermediates, in particular the Schiff base of formula I (or Ia), for example, compound M, can be used to purify Saxagliptin and salts thereof. In particular, the compounds of Formula I (or Ia) and Formula M are especially useful as intermediates in the purification of Saxagliptin, polymorphs thereof, in particular Saxagliptin hydrates (especially Forms H-1 and H0.5-2, and particularly Form H-1) and Saxagliptin salts and polymorphs thereof (particularly Saxagliptin HCl). In addition, the intermediates can used to directly prepare Saxagliptin salts, for example Saxagliptin HCl.

The novel Saxagliptin Schiff bases, in particular the Schiff bases of formula I and formula Ia, for example, compound M, have advantageous properties selected from at least one of: chemical purity, flowability, solubility, morphology or crystal habit and stability—such as storage stability. Schiff bases of formula I and formula Ia, and in particular crystalline compound form M of the present invention has advantageous enhanced chemical stability, for example when compared to Saxagliptin monohydrate form H-1.

A crystal form may be referred to herein as being characterized by graphical data "as depicted in" a Figure. Such data include, for example, powder X-ray diffractograms, FT-IR spectra and solid state NMR spectra. The skilled person will understand that such graphical representations of data may be subject to small variations, e.g., in peak relative intensities and peak positions due to factors such as variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms.

A crystal form (or polymorph) may be referred to herein as substantially free of any other crystalline (or polymorphic) forms. As used herein in this context, the expression "substantially free" will be understood to mean that the crystalline form contains 20% or less, 10% or less, 5% or less, 2% or less, or 1% or less of any other form of the subject compound as measured, for example, by powder XRD. Thus, polymorphs of Saxagliptin Schiff bases, Saxagliptin or Saxagliptin hydrochloride described herein as substantially free of any other polymorphic forms would be understood to contain greater than 80% (w/w), greater than 90% (w/w), greater than 95% (w/w), greater than 98% (w/w), or greater than 99% (w/w) of the subject polymorphic form of Saxagliptin or Saxagliptin hydrochloride. Accordingly, in some embodiments of the invention, the described polymorphs of Saxagliptin or Saxagliptin hydrochloride may contain from 1% to 20% (w/w), from 5% to 20% (w/w), or from 5% to 10% (w/w) of one or more other crystal forms of Saxagliptin or Saxagliptin hydrochloride.

As used herein, the term crystalline Saxagliptin monohydrate form H-1 refers to a crystalline Saxagliptin monohydrate form H-1 (e.g. as disclosed in US 2009/0054303) characterized by suitable analytical techniques, such as: a powder XRD pattern having peaks at 12.4, 13.3, 13.6, 14.7, 16.2, 18.2, 19.9, 20.9, 21.9 and 22.4 degrees 2-theta±0.1 degrees 2-theta, a powder XRD pattern substantially as depicted in FIG. 2 or FIG. 11; a FT-IR pattern substantially as depicted in FIG. 3, or combinations of these analytical data.

As used herein, the term crystalline Saxagliptin hemihydrate form H0.5-2 refers to a crystalline Saxagliptin hemihydrate form H0.5-2 (e.g. as disclosed in US 2009/0054303) characterized by analytical data such as: a powder XRD pattern substantially as depicted in FIG. 4, a FT-IR pattern substantially as depicted in FIG. 5, a selection of characteristic peaks from the FIG. 4 powder XRD pattern or the FIG. 5 FT-IR pattern that distinguish form H0.5-2 from other forms of crystalline Saxagliptin hemihydrate, or combinations of these analytical data.

Unless stated otherwise, the powder XRD peaks referred to herein were measured using a Cu radiation source having a wavelength of 1.54184 Å.

Unless stated otherwise, the HPLC peak % referred to herein were measured using a UV detection having a wavelength of 220 nm.

As used herein, the expression "Room temperature" or "RT" refers to a temperature from about 20° C. to about 30° C. Usually, room temperature ranges from about 20° C. to about 25° C.

As used herein, the expression "atmospheric pressure" refers to local atmospheric pressure, i.e., a pressure of about 1 atm or about 760 mmHg As used herein, the term "Overnight" refers to a time period of from about 15 to about 20 hours, typically between about 16 to about 20 hours.

As used herein, and unless stated otherwise, the term "anhydrous" in relation to crystalline Saxagliptin relates to a crystalline Saxagliptin which contains not more than 1%, preferably not more than 0.5% (w/w) of either water or organic solvents as measured by TGA.

As used herein, the term "wet crystalline form" refers to a polymorph that was not dried using any conventional techniques to remove residual solvent.

As used herein, the term "dry crystalline form" refers to a polymorph that was dried using any conventional techniques, e.g., vacuum drying to remove residual solvent.

The invention encompasses Saxagliptin Schiff bases.

In one embodiment the invention encompasses Saxagliptin Schiff bases of Formula I (wherein the stereochemistry is not defined):

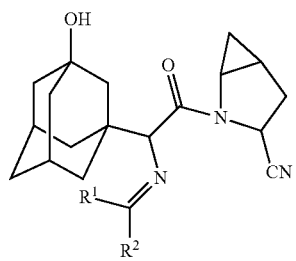

Formula I wherein $R^1$ is —H or $C_{1-4}$ alkyl and $R^2$ is H or $C_{1-4}$ alkyl, phenyl or substituted phenyl, wherein phenyl may be substituted with, for example, $C_{1-4}$ alkyl, halogen, or $C_{1-4}$ alkoxy. According to some embodiments, phenyl may be substituted with one, two or three groups, which may be the same or different, selected from C1-4 alkyl, halogen (particularly Cl, Br or I, more preferably Cl or Br), and C1-4 alkoxy.

In particular, the invention encompasses Saxagliptin Schiff bases of the following formula I (wherein the stereochemistry is not defined):

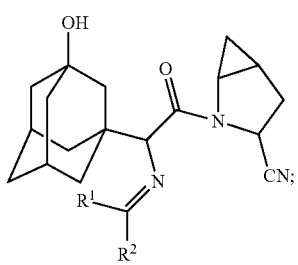

Formula I wherein $R^1$ is —H or $C_{1-4}$ alkyl and $R^2$ is $C_{1-4}$ alkyl, phenyl or substituted phenyl, wherein phenyl may be substituted with, for example, $C_{1-4}$ alkyl, halogen (particularly Cl, Br or I, more preferably Cl or Br), or $C_{1-4}$ alkoxy. Preferably the substituents on the phenyl are $C_{1-4}$ alkyl or $C_{1-4}$ alkoxy. Preferably, $R^1$ is $C_{1-4}$ alkyl. $R^2$ is preferably $C_{1-4}$ alkyl or unsubstituted phenyl. More preferably, $R^1$ and $R^2$ are each independently selected from $C_{1-4}$ alkyl. In preferred embodiments, $R^1$ and $R^2$ are the same, and are preferably selected from $C_{1-4}$ alkyl, particularly $C_{1-3}$ alkyl and particularly methyl or ethyl. Preferably, $R^1$ and $R^2$ are methyl.

In preferred embodiment, the present invention encompasses Saxagliptin Schiff bases having fixed stereochemistry according to the following formula Ia:

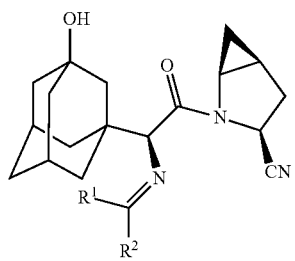

Formula Ia wherein $R^1$ is —H or $C_{1-4}$ alkyl and $R^2$ is H or $C_{1-4}$ alkyl, phenyl or substituted phenyl, wherein phenyl may be substituted with, for example, $C_{1-4}$ alkyl, halogen (particularly Cl, Br or I, more preferably Cl or Br), or $C_{1-4}$ alkoxy. Preferably the substituents on the phenyl are $C_{1-4}$ alkyl or $C_{1-4}$ alkoxy. Preferably, $R^1$ is $C_{1-4}$ alkyl. $R^2$ is preferably $C_{1-4}$ alkyl or unsubstituted phenyl. More preferably, $R^1$ and $R^2$ are each independently selected from $C_{1-4}$ alkyl. In preferred embodiments, $R^1$ and $R^2$ are the same, and are preferably selected from $C_{1-4}$ alkyl, particularly $C_{1-3}$ alkyl and particularly methyl or ethyl. Preferably, $R^1$ and $R^2$ are methyl.

In more preferred embodiment, the present invention encompasses Saxagliptin Schiff bases having fixed stereochemistry according to the following formula Ia:

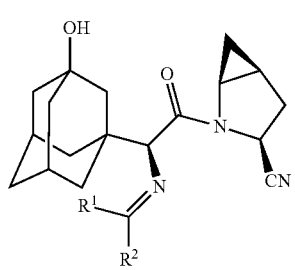

Formula Ia wherein $R^1$ is —H or $C_{1-4}$ alkyl and $R^2$ is $C_{1-4}$ alkyl, phenyl or substituted phenyl, wherein phenyl may be substituted with, for example, $C_{1-4}$ alkyl, halogen (particularly Cl, Br or I, more preferably Cl or Br), or $C_{1-4}$ alkoxy. Preferably the substituents on the phenyl are $C_{1-4}$ alkyl or C1-4 alkoxy. Preferably, $R^1$ is $C_{1-4}$ alkyl. $R^2$ is preferably $C_{1-4}$ alkyl or unsubstituted phenyl. More preferably, $R^1$ and $R^2$ are each independently selected from $C_{1-4}$ alkyl. In preferred embodiments, $R^1$ and $R^2$ are the same, and are preferably selected from $C_{1-4}$ alkyl, particularly $C_{1-3}$ alkyl and particularly methyl or ethyl. Preferably, $R^1$ and $R^2$ are methyl.

The invention particularly encompasses (1S,3S,5S)-2-[(2S)-2-propan-2-ylideneamino-2-(3-hydroxy-1-adamantyl)acetyl]-2-azabicyclo[3.1.0]hexane-3-carbonitrile, referred to as Compound M:

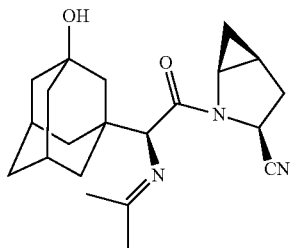

Compound M

The compound of Formula M can be characterized by data such as NMR, FT-IR, MS or combinations thereof.

Compound M can be characterized by data selected from: $^1$H NMR (CDCl$_3$, 600 MHz) having peaks at 0.83-0.89, 0.92-0.97, 1.50-1.73, 1.80, 1.85, 2.10, 2.23, 2.30, 2.42-2.49, 3.82, 3.97 and 5.00 ppm; a $^{13}$C NMR (CDCl$_3$, 150 MHz,) having peaks at 12.1, 17.6, 19.6, 29.7, 29.9, 30.6, 30.7, 35.6, 37.0, 38.0, 38.5, 41.6, 44.7, 44.8, 45.7, 47.1, 69.1, 73.7, 120.0, 169.8 and 169.9 ppm; and combinations thereof.

The compounds of Formula I, Ia, and particularly Compound M can be in an isolated form, preferably in a crystalline form. As used herein, the term "isolated" in reference to Formula I, Ia and compound M corresponds to compounds of Formula I, Ia and Compound M that are physically separated, e.g. from the reaction mixture wherein they are formed. Preferably the Compounds of Formula I, Ia and Compound M contain 5% or less, preferably 4% or less, more preferably 2% or less, or 1% or less, and most preferably 0.5% or less of the starting saxagliptin.

Preferably, the compounds of Formula I, Ia and compound M each have purities (e.g. as measured by HPLC or by wt %) of at least about 95%, more preferably at least about 97%, still more preferably at least about 98%, and most preferably at least about 99%. Preferably, the compounds of Formula I, Ia and compound M each contain less than about 2% (e.g. as measured by HPLC or by wt %), preferably less than about 1%, more preferably less than about 0.5% and most preferably less than about 0.4% of the cyclic amidine impurity of saxagliptin:

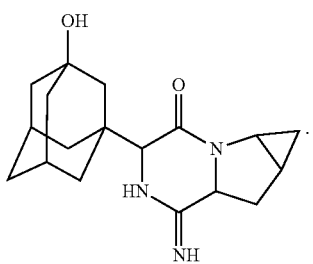 [SMILES: N=C1NC(C23CC4CC(CC(O)(C4)C2)C3)C(=O)N2C1CC1CC12]

The Schiff bases of Formula I, Ia, and Compound M are stable to storage. In particular, the compounds of Formula I, Ia and Compound M and their crystalline forms according to the invention are stable under typical room conditions (room temperature, atmospheric pressure, relative humidity of about 40%). In particular, compounds of formula I, Ia, and compound M and crystalline forms thereof are stable to the intra-molecular cyclization known to occur for Saxagliptin to form the cyclic amidine impurity above (see for example WO 2005/117841). Preferably, compounds of Formula I and Ia, and particularly Compound M, are stable to storage:

(i) at 40° C. and 40% relative humidity over a period of at least 1 month
(ii) at 40° C. and 40% relative humidity over a period of at least 2 months
(iii) at 50° C. and 0% relative humidity over a period of at least 1 month
(iv) at 50° C. and 0% relative humidity over a period of at least 2 months By "stable to storage" it is meant that the % purity (e.g. by weight or by HPLC) of the Compound of Formula I, Ia or Compound M after storage at the above conditions [preferably after storage at conditions (iii) or (iv), and more preferably at condition (iv)], decreases by not more than about 0.8%, preferably no more than about 0.6%, typically no more than about 0.4% and more preferably no more than about 0.25% (percentage of the purity after manufacture (time zero). Preferably, the term "stable to storage" means that the Compound of Formula I, Ia or Compound M after storage at the above conditions [preferably after storage at conditions (iii) or (iv), and more preferably at condition (iv)] has a purity (e.g. by HPLC or by weight) of at least about 98%, preferably at least about 98.5%, and more preferably at least about 99%.

Typically, immediately after manufacture (time zero) the amount of the cyclic amidine impurity is 0.4% (by weight or by HPLC) or less, more preferably about 0.3% or less, and most preferably about 0.2% or less. Thus, preferably, by "stable to storage", it is meant that the % (by weight or by HPLC) of the cyclic amidine impurity after storage at the above conditions [preferably after storage at conditions (iii) or (iv), and more preferably at condition (iv)] is about 0.8% or less, preferably about 0.7% or less, more preferably about 0.6% or less, and most preferably about 0.4% or less.

In one embodiment the invention encompasses crystalline compound M, characterized by data selected from: a powder XRD pattern with peaks at 11.2, 12.6, 14.0, 16.6, and 19.5±0.2 degrees 2-theta; a powder XRD pattern substantially as depicted in FIG. 7; a solid state NMR with peaks at 171.43, 42.13 and 29.83 ppm±0.2 ppm; a solid state NMR pattern substantially as depicted in FIG. 13; and combinations thereof.

The above crystalline compound M can be further characterized by data selected from: additional powder XRD peaks at 14.5, 19.1 and 30.2±0.2 degrees 2-theta; a solid state NMR with additional peaks at 43.59 and 37.23 ppm±0.2 ppm; a FT-IR spectrum substantially as depicted in FIG. 8; a FT Raman spectrum substantially as depicted in FIG. 9; a DSC thermogram substantially as depicted in FIG. 10; and combinations thereof.

The compound of formula I or Ia and Compound M can be prepared by reacting saxagliptin base with an aldehyde or ketone of formula:

wherein $R^1$ and $R^2$ have the same meanings as mentioned above for Formula I. Thus, $R^1$ is —H or $C_{1-4}$ alkyl and $R^2$ is $C_{1-4}$ alkyl, phenyl or substituted phenyl, wherein phenyl may be substituted with, for example, $C_{1-4}$ alkyl, halogen (particularly Cl, Br or I, more preferably Cl or Br), or $C_{1-4}$ alkoxy. Preferably the substituents on the phenyl are $C_{1-4}$ alkyl or $C_{1-4}$ alkoxy. Preferably, $R^1$ is $C_{1-4}$ alkyl. $R^2$ is preferably $C_{1-4}$ alkyl or unsubstituted phenyl. More preferably, $R^1$ and $R^2$ are each independently selected from $C_{1-4}$ alkyl. In preferred embodiments, $R^1$ and $R^2$ are the same, and are preferably selected from $C_{1-4}$ alkyl, particularly $C_{1-3}$ alkyl and particularly methyl or ethyl. Preferably, $R^1$ and $R^2$ are methyl.

Typically, the compound of formula I (or Ia), and in particular compound M, and their crystalline forms can be prepared by a process comprising dissolving or suspending Saxagliptin base in a ketone solvent, such as methyl ethyl ketone ("MEK"), methyl isobutyl ketone ("MIBK"), acetophenone or acetone; or an aldehyde solvent, for example, formaldehyde, acetaldehyde, or benzaldehyde; and precipitating the compound of formula I (or Ia). The process comprises providing a solution or a suspension of Saxagliptin base in the above described solvents, preferably at about room temperature, and precipitating. The solution or the suspension can be maintained for a period such as from about 3 hours to about 48 hours, preferably from about overnight to about 24 hours, at a temperature such as room temperature. The Compound of formula I (or Ia) can then be recovered from the suspension, for example by filtering and drying. Drying can be done under vacuum, for example on a temperature such as about room temperature to about 40° C., for about 2 hours.

In particular, the invention encompasses a process for the preparation of compound M and its crystalline form; said process comprises dissolving or suspending Saxagliptin base in the above described solvents, preferably in acetone, and precipitating compound M.

Compound M can also be prepared by a process comprising maintaining Saxagliptin, preferably amorphous Saxagliptin in an acetone atmosphere. The process can be done in a desiccator, at a temperature such as room temperature, for a period of about 12 hours to about 48 hours, preferably 24 hours.

The Schiff bases of Saxagliptin, in particular the above described compounds of formula I (and Ia) and compound M, as well as their crystalline forms can be used to prepare and to purify Saxagliptin and salts thereof, for example, Saxagliptin HCl.

In one embodiment the invention encompasses the preparation of Saxagliptin, Saxagliptin salts and their polymorphic forms thereof by a process comprising preparing a Saxagliptin Schiff base, in particular Saxagliptin Schiff base of formula I or Ia, or compound M and converting that compound to Saxagliptin. The conversion process to prepare Saxagliptin and polymorphs thereof, in particular Saxagliptin hydrate, can comprise, hydrolysis of the Saxagliptin Schiff base as defined above. Typically, the hydrolysis is carried out by exposure of Saxagliptin Schiff base as defined above to water. The process can be done, for example, by maintaining compound M in a relative humidity (RH) of about 100%, for a period of about 24 hours; or alternatively, suspending compound M in water.

In another embodiment the invention encompasses the preparation of a Saxagliptin salt, by a process comprising:
a) dissolving preparing Saxagliptin Schiff base, in particular Saxagliptin Schiff base of formula I, Ia and compound M in a suitable solvent, preferably a water miscible solvent more preferably acetone;
b) adding an acid (preferably a mineral acid, and more preferably hydrochloric acid), and optionally water; and
c) recovering the Saxagliptin salt.

In particular, the invention encompasses a process for preparing Saxagliptin HCl comprising reacting a Schiff base according to Formula I or Ia, such as for example, compound M, and a sufficient amount of HCl. The process typically comprises dissolving compound M in a suitable solvent such as acetone or ethyl acetate; and adding HCl, preferably aqueous HCl, in an amount of from 1 to 2 mole equivalents, for example, about 1.1 mole equivalents, to obtain a suspension, from which Saxagliptin HCl precipitates. Optionally, water can be added to the suspension prior to the recovery of Saxagliptin HCl.

Saxagliptin HCl can be recovered from the suspension, for example by filtering and drying. Drying can comprise air drying.

The present invention encompasses Schiff bases of Saxagliptin, in particular the above described compounds of formula I (and Ia), and compound M, for use in preparation of (a) Saxagliptin; (b) Saxagliptin salts, preferably Saxagliptin hydrochloride; and (c) formulations of Saxagliptin or Saxagliptin salts, preferably Saxagliptin hydrochloride The present invention also encompasses Schiff bases of Saxagliptin, in particular the above described compounds of formula I (and Ia) and compound M, for use in preparation of pharmaceutical formulations. The pharmaceutical formulations can be used for the treatment of type 2 diabetes In one embodiment the invention encompasses crystalline Saxagliptin, designated form FI. Form FI can be characterized by a powder XRD pattern having peaks at 7.4, 8.6, 15.3, 17.1, and 18.0 degrees 2-theta±0.2 degrees 2-theta. Form FI can be further characterized by additional powder XRD peaks at 16.6, 21.7, 24.1, and 27.0 degrees 2-theta±0.2 degrees two-theta.

Alternatively Saxagliptin form FI can be characterized by a powder XRD pattern with peaks at 7.4, 8.6, 15.3, 16.6, 17.1, 18.0, 21.7, 24.1, and 27.0 degrees two theta±0.2 degrees two theta. In addition, Saxagliptin form FI can be characterized by any combination of the above data.

Form FI can be in a mixture with crystalline form H1. This mixture can be characterized by a powder XRD pattern substantially as depicted in FIG. 1. Typically, the presence of form H1 in the mixture can be can be detected by powder XRD using the peaks at 13.2, 13.6, and 18.1 degrees two theta±0.2 degrees two theta.

Saxagliptin form FI can be used for the manufacture of a medicament for the treatment of type 2 diabetes.

The invention also encompasses novel processes for the preparation of crystalline Saxagliptin monohydrate form H-1, crystalline Saxagliptin hemihydrate form H0.5-2 and a mixture of crystalline Saxagliptin monohydrate form H-1 and crystalline Saxagliptin hemihydrate form H0.5-2.

The process for preparing crystalline Saxagliptin monohydrate form H-1 comprises maintaining amorphous Saxagliptin in an atmosphere of a solvent selected from ethanol 96% (v/v), dibutyl ether, and water at about 80% to about 100% relative humidity; at a temperature of about room temperature for a period of about 24 hours to about 48 hours.

The process for preparing crystalline Saxagliptin hemihydrate form H0.5-2 comprises maintaining amorphous Saxagliptin in an atmosphere of ethyl acetate at a temperature of about room temperature for a period of about 24 hours.

The process for preparing a mixture of crystalline Saxagliptin mono-hydrate form H-1 and crystalline Saxagliptin hemihydrate form H0.5-2 comprises maintaining amorphous Saxagliptin in an atmosphere of a solvent selected from: toluene, diethyl ether, methyl acetate, isobutyl acetate, 1-octanol, anisole and 1-butanol; at a temperature of about room temperature for a period of about 48 hours.

The present invention further encompasses 1) a pharmaceutical composition comprising any one or combination of solid state forms, as described above, and at least one pharmaceutically acceptable excipient; and 2) the use of any one or combination of the above-described solid state Forms, in the manufacture of a pharmaceutical composition. The pharmaceutical composition can be useful for the treatment of type 2 diabetes. The present invention also provides crystalline forms as described above for use as a medicament, preferably for the treatment of type 2 diabetes.

Having described the invention with reference to certain preferred embodiments, other embodiments will become apparent to one skilled in the art from consideration of the specification. The invention is further defined by reference to the following examples describing in detail the preparation of the composition and methods of use of the invention. It will be apparent to those skilled in the art that many modifications, both to materials and methods, may be practiced without departing from the scope of the invention.

Powder X-Ray Diffraction Method

After being powdered using mortar and pestle, the sample was applied directly on a silicon plate holder. The X-ray powder diffraction pattern was measured with a Philips X'Pert PRO X-ray powder diffractometer, equipped with a Cu irradiation source=1.54184 Å (Angström), X'Celerator (2.022° 2θ) detector. Scanning parameters: angle range: 3-40 deg., step size 0.0167, time per step 37 s, continuous scan. In some samples, silicon powder was added as an internal standard, the position of the silicon (Si) peak is indicated in the relevant figures. The described peak positions for Saxagliptin form FI and compound M were determined using silicon powder as an internal standard in an admixture with the sample measured. The position of the silicon (Si) peak was corrected to the silicon theoretical peak: 28.45 degrees two theta, and the positions of the measured peaks were corrected respectively. No correction was performed on the diffractograms depicted in the figures.

FT-IR Method

IR spectra were recorded on Nicolet 6700 FT-IR spectrometer equipped with KBr beam-splitter and DTGS detector. For each spectrum 16 scans were recorded over the range 4000-400 cm-1, at resolution of 4.0 cm-1. Samples were prepared as KBr pellets. Air (empty sample compartment) was used for background spectrum acquisition.

FT Raman Method

Raman spectrum was acquired on a Nicolet 6700 interferometer, equipped with an NXR FT-Raman module. A Nd-YAG laser (1064 nm, 500 mW) was used to excite the sample. The spectrometer utilizes a CaF2 beamsplitter and a liquid nitrogen cooled Ge detector. The spectrum was recorded at resolution of 4 cm-1. An NMR glass tube was used as sample holder.

Differential Scanning Calorimetry DSC Method

DSC analysis was performed on Q 1000 MDSC TA instruments with heating rate of 10° C./min, under nitrogen flow of 50 ml/min. A hermetic aluminum, closed pan with hole was used, and the sample mass was about 1-5 mg.

Nuclear Magnetic Resonance (NMR) Method 1H (600 MHz) and 13C (APT) (150 MHz) NMR spectra were recorded on Bruker Avance DRX 600 NMR spectrometer. CDCl3 was used as a solvent. Chemical shifts (δ), in ppm, are referred to TMS as internal standard.

Solid State NMR Method

Solid-state 13C NMR spectra were recorded with variable amplitude cross polarization, magic angle spinning and high power proton decoupling using a BRUKER Avance II+ spectrometer operating at 125 MHz and ambient temperature (about 25° C.—not controlled). A probe using 4 mm o.d. zirconia rotors was employed. The operation conditions were: contact time: 2 ms; recycle delay: 25 s 256 scans; spin rate of 11 kHz. Chemical shifts were referenced via a replacement sample of glycine (carboxyl carbon chemical shift assigned as 176.03 ppm relative to the signal of tetramethylsilane).

High-Performance Liquid Chromatography (HPLC) Method
Instrumental and Chromatographic Conditions
Instrument: HPLC system equipped with UV detector.
  Flow rate: about 1 mL/min
  Injection volume: about 10 µL
  Column: Waters XBridge C8, 150 mm×4.6 mm, 3.5 µm
  Column temperature: 25° C.
  Detector: DAD (UV) at wavelengths 220 nm
  Mobile phase: Gradient elution with Solution A and Solution B (see Table 1)
    Solution A: Buffer solution. Dissolve in water about 24.0 g of sodium octyl-1-sulfonate in 1000 mL volumetric flask, make up to the volume with water and adjust pH to 3.3 with phosphoric acid.
    Solution B: Acetonitrile, HPLC grade

TABLE 1

Gradient elution

| t [min] | % B | flow [mL/min] |
|---|---|---|
| 0.0 | 15 | 1.00 |
| 10.0 | 60 | 1.00 |
| 10.1 | 60 | 0.90 |
| 18.0 | 75 | 0.90 |
| 25.0 | 75 | 0.90 |

Stop time: 25 minutes
Post time: 5 minutes
Diluent: Prepare a solution of 25% acetonitrile, 25% methanol, and 50% of the buffer solution (the one that is used in gradient elution).
The Following Chemicals (or Equivalent) Should Be Used:
  Sodium Octyl-1-sulfonate, 99%
  Phosphoric Acid, p.a.
  Acetonitrile, HPLC grade
Preparation of Solutions for Impurities:
  1. Blank: Use the diluent.
  2. Sample preparation: Prepare SXG sample solution with concentration of about 1.0 mg/mL prepare in duplicate
Procedure
  Achieve a stable baseline in HPLC system.
  Inject diluent
  Inject sample solution into the chromatograph

EXAMPLES

Example 1

Preparation of Starting Material: Amorphous Saxagliptin

Sdf (1S,3S,5S)-2-[(2S)-2-[(1,1-dimethoxy)carbonyl]amino-2-(3-hydroxy-1-adamantyl)acetyl]-2-azabicyclo[3.1.0]hexane-3-carbonitrile ("Boc-Saxagliptin") (5.25 g; 12.63 mmol) was dissolved in 2-PrOH (6.7 mL) and water (6.3 mL) was added. HCl (0.21 mL, 2.52 mmol, conc.) was added at room temperature with stirring. The resulting mixture was heated to 65° C. and conc. HCl (1.27 mL; 15.14 mmol) was added dropwise to the reaction mixture over 5 minutes while maintaining the temperature at 65° C. The reaction mixture was stirred at 65° C. for 2 hours, then cooled down to room temperature which resulted in formation of a precipitate. Water (10.5 mL) and dichloromethane (31.5 mL) were added to the reaction mixture followed by addition of 10M NaOH (1.10 mL; 12.67 mmol) and 1.05 mL of water for washing. Potassium carbonate (25% wt. solution, 5.6 mL) was added to adjust the pH to 9. This was followed by addition of water (1.05 mL) and NaCl (6.56 g; 0.115 mol). At this point, the pH dropped to 8.48 so an additional amount of K2CO3 solution was added (1.0 mL) to adjust pH back to 9. The mixture was then stirred at room temperature for 30 minutes after which the two-phase mixture was separated. The separated water layer was extracted with dichloromethane (4×50 mL). The organic layers were combined and evaporated to dryness under reduced pressure yielding 4.11 g of crude Saxagliptin.

The crude Saxagliptin residue was purified by flash chromatography in $CH_2Cl_2$/MeOH/$NH_3$ (25% wt. sol.) 5:1:0.1 as eluent. Fractions containing the pure product were combined and evaporated to dryness under reduced pressure with moderate heating (40-43° C.), yielding 3.43 g (86%) of Saxagliptin as a white foam.

Example 2

Preparation of Crystalline Saxagliptin Form FI in a Mixture with Crystalline Saxagliptin Form H-1

Amorphous Saxagliptin was placed in a Petri dish in a desiccator in the atmosphere of 2-propanol at room temperature. After 24 h the sample was tested by powder XRD and a new crystalline form of Saxagliptin (FI) was found in a mixture with crystalline Saxagliptin monohydrate H-1.

Example 3

Preparation of Crystalline Saxagliptin Monohydrate Form H-1

Amorphous saxagliptin was placed in a Petri dish in a desiccator in the atmosphere of ethanol (96%, commercial denatured ethanol) at room temperature. After 24 hours the sample was tested by powder XRD. Crystalline saxagliptin monohydrate H-1 was found.

Example 4

Preparation of Crystalline Saxagliptin Monohydrate Form H-1

Amorphous saxagliptin was placed in a Petri dish in a desiccator in the atmosphere of dibutyl ether at room temperature. After 48 hours the sample was tested by powder XRD. Crystalline saxagliptin monohydrate H-1 was found.

Example 5

Preparation of Crystalline Saxagliptin Monohydrate Form H-1

Amorphous saxagliptin was placed in a Petri dish in a desiccator in the atmosphere of water, 100% relative humidity (determined by digital hygrometer) at room temperature. After 24 hours the sample was tested by powder XRD. Crystalline saxagliptin monohydrate H-1 was found.

Example 6

Preparation of Crystalline Saxagliptin Monohydrate Form H-1

Amorphous saxagliptin was placed in a Petri dish in a desiccator in the atmosphere of water, 80% relative humidity (determined by digital hygrometer) at room temperature. After 24 hours the sample was tested by powder XRD. Crystalline saxagliptin monohydrate H-1 was found.

Example 7

Preparation of Crystalline Saxagliptin Hemihydrate Form H0.5-2

Amorphous saxagliptin was placed in a Petri dish in a desiccator in the atmosphere of ethyl acetate at room temperature. After 24 hours the sample was tested by powder XRD. Crystalline saxagliptin hemihydrate H0.5-2 was found.

Example 8

Preparation of a Mixture of Crystalline Saxagliptin Monohydrate Form H-1 and Crystalline Saxagliptin Hemihydrate Form H0.5-2

Amorphous saxagliptin was placed in a Petri dish in a desiccator in the atmosphere of toluene at room temperature. After 48 hours the sample was tested by powder XRD. Crystalline saxagliptin hemihydrate H0.5-2 and monohydrate H-1 were found in a mixture Example 9

Preparation of a Mixture of Crystalline Saxagliptin Monohydrate Form H-1 and Crystalline Saxagliptin Hemihydrate Form H0.5-2

Amorphous saxagliptin was placed in a Petri dish in a desiccator in the atmosphere of diethyl ether at room temperature. After 48 hours the sample was tested by powder XRD. Crystalline saxagliptin hemihydrate H0.5-2 and monohydrate H-1 were found in a mixture.

Example 10

Preparation of a Mixture of Crystalline Saxagliptin Monohydrate Form H-1 and Crystalline Saxagliptin Hemihydrate Form H0.5-2

Amorphous saxagliptin was placed in a Petri dish in a desiccator in the atmosphere of methyl acetate at room temperature. After 48 hours the sample was tested by powder XRD. Crystalline saxagliptin hemihydrate H0.5-2 and monohydrate H-1 were found in a mixture.

Example 11

Preparation of a Mixture of Crystalline Saxagliptin Monohydrate Form H-1 and Crystalline Saxagliptin Hemihydrate Form H0.5-2

Amorphous saxagliptin was placed in a Petri dish in a desiccator in the atmosphere of iso-butyl acetate at room temperature. After 48 hours the sample was tested by powder XRD. Crystalline saxagliptin hemihydrate H0.5-2 and monohydrate H-1 were found in a mixture.

Example 12

Preparation of a Mixture of Crystalline Saxagliptin Monohydrate Form H-1 and Crystalline Saxagliptin Hemihydrate Form H0.5-2

Amorphous saxagliptin was placed in a Petri dish in a desiccator in the atmosphere of 1-octanol at room temperature. After 48 hours the sample was tested by powder XRD. Crystalline saxagliptin hemihydrate H0.5-2 and monohydrate H-1 were found in a mixture.

Example 13

Preparation of a Mixture of Crystalline Saxagliptin Monohydrate Form H-1 and Crystalline Saxagliptin Hemihydrate Form H0.5-2

Amorphous saxagliptin was placed in a Petri dish in a desiccator in the atmosphere of anisole at room temperature. After 48 hours the sample was tested by powder XRD. Crystalline saxagliptin hemihydrate H0.5-2 and monohydrate H-1 were found in a mixture.

Example 14

Preparation of a Mixture of Crystalline Saxagliptin Monohydrate Form H-1 and Crystalline Saxagliptin Hemihydrate Form H0.5-2

Amorphous saxagliptin was placed in a Petri dish in a desiccator in the atmosphere of 1-butanol at room temperature. After 48 hours the sample was tested by powder XRD. Crystalline saxagliptin hemihydrate H0.5-2 and monohydrate H-1 were found in a mixture.

Example 15

Preparation of Crystalline (1S,3S,5S)-2-[(2S)-2-propan-2-ylideneamino-2-(3-hydroxy-1-adamantyl) acetyl]-2-azabicyclo[3.1.0]hexane-3-carbonitrile (Compound M)

Saxagliptine form H-1 (100 mg) was suspended in acetone (1 ml). The suspension was stirred for 24 hours at room temperature, after which it was filtered and dried on air, yielding 54 mg of crystalline product $^1$H NMR (CDCl$_3$, 600 MHz) δ 0.83-0.89 (m, 1H), 0.92-0.97 (m, 1H), 1.50-1.73 (m, 12H), 1.80 (m, 1H), 1.85 (s, 3H), 2.10 (s, 3H), 2.23 (m, 2H), 2.30 (m, 1H), 2.42-2.49 (m, 1H), 3.82 (m, 1H), 3.97 (m, 1H), 5.00 (m, 1H).

$^{13}$C NMR (CDCl$_3$, 150 MHz,) δ 12.1, 17.6, 19.6, 29.7, 29.9, 30.6, 30.7, 35.6, 37.0, 38.0, 38.5, 41.6, 44.7, 44.8, 45.7, 47.1, 69.1, 73.7, 120.0, 169.8, 169.9.

Example 16

Preparation of Crystalline (1S,3S,5S)-2-[(2S)-2-propan-2-ylideneamino-2-(3-hydroxy-1-adamantyl) acetyl]-2-azabicyclo[3.1.0]hexane-3-carbonitrile (Compound M)

Amorphous saxagliptin was placed in a Petri dish in a desiccator in the atmosphere of acetone at room temperature. After 24 hours the sample was tested by powder XRD. Crystalline compound M was obtained.

Example 17

Preparation of Crystalline Saxagliptin Monohydrate Form H-1

Crystalline compound M was placed in a Petri dish in a desiccator in the atmosphere of water, 100% relative humidity at room temperature. After 24 hours the sample was tested by powder XRD. Crystalline saxagliptin monohydrate H-1 was found, powder XRD as depicted in FIG. 11, sample was measured using silicone standard. No correction was performed on the figure.

Example 18

Preparation of Saxagliptin Base

Purified Boc-Saxagliptin (15.9 g) was dissolved in 2-PrOH, p.a. (95.4 mL). To this solution, an equal volume of water (95.4 mL) was added. The measured pH was 8.2. The pH of the solution was adjusted to 1.0 by the addition of 6.4 mL of conc. HCl. The resulting solution was heated to reflux and stirred at reflux for 4 hours. After this time all of the Boc-Saxagliptin was converted to Saxagliptin base (HPLC). The solution was then cooled to room temperature and dichloromethane (DCM) (159 mL) was added. After the DCM was added, the measured pH was 1.03. The pH was adjusted to 9.03 by adding 70.8 mL of 1M NaOH. The layers of the resulting 2-phase mixture were separated. To the upper (water layer) was added 62 g of NaCl, and the resulting aqueous phase was washed twice with 96 mL of DCM. The multiple obtained DCM layers were combined, dried over MgSO$_4$ and evaporated to dryness to provide 12.3 g of a white foamy product.

Example 19

Preparation of Saxagliptin Schiff Base

Compound M

Saxagliptin base (10.2 g) was dissolved in 33 mL of acetone, p.a. (dried on MgSO$_4$) at room temperature. The resulting clear solution was left stirring overnight in a closed flask at room temperature. An off white crystalline product was obtained. The product was filtered off and dried at 40° C./0 mbar for 2 hours. (Yield=63.02%).

Example 20

Preparation of Boc-Saxagliptin (S)—N-Boc-3-hydroxyadamantylglycine-L-cis-4,5-methanoprolinamide ("AMSG") (23 g, 53.05 mmol) was dissolved in technical distilled dichloromethane (DCM) (115 mL) at 0° C. in three necked round bottom flask. A colorless to light yellow solution was obtained. To this solution, triethylamine (22.1 ml, 159.15 mmol) was added without any visible change, and the resulting reaction mixture was stirred for 30 minutes at 0° C. During a time period of 30 minutes, trichloroacetyl chloride (7.7 ml, 68.9 mmol) in technical distilled DCM (69 ml) was added dropwise at 0° C. During this addition white smoke was observed. The temperature did not rise above 7° C. Five minutes after the addition of trichloroacetyl chloride was complete, the reaction mixture was heated to approximately 10° C., and 230 ml of H$_2$O was added, and the mixture was well stirred. The layers were separated in a separation funnel. To the upper (water layer) NaCl was added (⅔ saturated solution of NaCl), and this aqueous layer was extracted twice with 50 ml of technical distilled DCM. The multiple DCM layers were combined, washed once with 140 ml of 20% solution of KHCO$_3$, dried over MgSO$_4$, and evaporated to dryness to provide 24 g of a white to off-white foamy product.

Example 21

Purification of Crude Boc-Saxagliptin

Boc-Saxagliptin (23.8 g)) crude was suspended in 58 ml of 2-PrOH, p.a. The suspension was heated while stirring and heating to reflux, and a clear solution was obtained. The clear solution was removed from reflux and 185 ml of water was added dropwise with stirring, to form a suspension. The suspension was stirred for an additional 2 hours at room temperature and crystals formed. The crystals were filtered off and dried at 40° C./0 mbar for 2 hours to provide 15.9 g of white solid. (Yield=66.8%)

Example 22

Preparation of Saxagliptin Monohydrate Form H-1

The Schiff base (Compound M, 7.27 g) was suspended in 25 ml of water. The obtained suspension was stirred overnight at room temperature in a closed flask. The product was filtered off and dried at 40° C./0 mbar for 2 hours. (Yield=80.1%) HPLC 100%, Powder XRD—H-1

Example 23

Preparation of Saxagliptin Hydrochloride Starting from Compound M

The Schiff base of Saxagliptin (compound M, 500 mg) was dissolved in acetone (4 ml), and HCl (0.131 ml, 36.5%) was added. The resulting suspension was stirred for 30 min. Water (0.6 ml) was added and continued stirring for additional 45 min. The suspension was then filtered yielding saxagliptin hydrochloride, form H2-1 (375 mg).

Example 24

Preparation of Amorphous Saxagliptin Base

Saxagliptin monohydrate (300 mg) was dissolved in water (40 ml) and lyophilized yielding amorphous saxagliptin.

Example 25

Stability of Crystalline Compound M and Saxagliptin Monohydrate Form H-1

Samples of crystalline compound M and Saxagliptin monohydrate form H-1 were prepared and the amount of Saxagliptin and the amount of cyclic amidine were measured by HPLC at time zero (=time 0). Samples of crystalline compound M and Saxagliptin monohydrate form H-1 were maintained for 2 weeks, 1 month and 2 months, at the conditions described in the following table. Afterwards, the amount of Saxagliptin and the amount of cyclic amidine was measured by HPLC.

What is claimed:

1. A Saxagliptin Schiff base according to Formula I, wherein the stereochemistry is not defined:

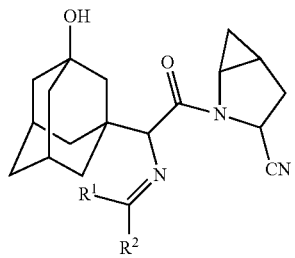

Formula I wherein $R^1$ is —H or $C_{1-4}$ alkyl and $R^2$ is —H or $C_{1-4}$ alkyl, phenyl or substituted phenyl.

2. The Saxagliptin Schiff base according to claim 1, wherein $R^1$ is —H or $C_{1-4}$ alkyl and $R^2$ is $C_{1-4}$ alkyl, phenyl or substituted phenyl.

3. The Saxagliptin Schiff base according to claim 1, having a structure according to formula Ia:

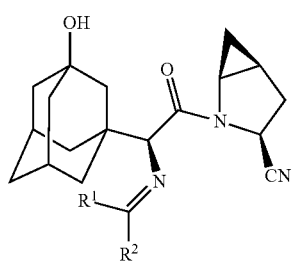

Formula Ia wherein $R^1$ is —H or $C_{1-4}$ alkyl and $R^2$ is —H or $C_{1-4}$ alkyl, phenyl or substituted phenyl.

4. The Saxagliptin Schiff base according to claim 3, wherein $R^1$ is —H or $C_{1-4}$ alkyl and $R^2$ is $C_{1-4}$ alkyl, phenyl or substituted phenyl.

5. The Saxagliptin Schiff base according to claim 4, wherein $R^1$ is $C_{1-4}$ alkyl.

6. The Saxagliptin Schiff base according to claim 5, wherein $R^2$ is $C_{1-4}$ alkyl or unsubstituted phenyl.

7. The Saxagliptin Schiff base according to claim 6, wherein $R^1$ and $R^2$ are each independently selected from $C_{1-4}$ alkyl.

8. The Saxagliptin Schiff base according to claim 7, wherein $R^1$ and $R^2$ are selected from $C_{1-4}$ alkyl.

| Condition - sample | Time 0 | 2 weeks | 1 month | 2 months |
|---|---|---|---|---|
| 50° C./0% RH Saxaglitpin base monohydrate, Form H-1 | CA = 0.50% SXG = 98.9% | CA = 1.2% SXG = 97.8% RRT1.14 = 0.4% | CA = 1.3% SXG = 96.9% RRT1.14 = 1.1% | CA = 2.1% SXG = 94.8% RRT1.14 = 2.51% |
| 50° C./0% RH Schiff base - crystalline Compound M | CA = 0.20% SXG = 99.6% | CA = 0.25% SXG = 99.6% | CA = 0.27% SXG = 99.4% | CA = 0.31% SXG = 99.4% |
| 40° C./40% RH Saxaglitpin base monohydrate, Form H-1 | CA = 0.50% SXG = 98.9% | CA = 4.0% SXG = 93.1% RRT1.14 = 2.1% | CA = 5.8% SXG = 86.8% RRT1.14 = 4.1% | CA = 11.5% SXG = 77.4% RRT1.14 = 7.7% |
| 40° C./40% RH Schiff base - crystalline Compound M | CA = 0.20% SXG = 99.6% | CA = 0.53% SXG = 99.0% | CA = 0.50% SXG = 99.0% | CA = 0.61% SXG = 99.0% |

CA = cyclic amidine,
SXG = Saxagliptin,
RH = relative humidity.

9. The Saxagliptin Schiff base according to claim 8, wherein $R^1$ and $R^2$ are methyl or ethyl.

10. The Saxagliptin Schiff base according to claim 9, wherein $R^1$ and $R^2$ are methyl.

11. The compound M:

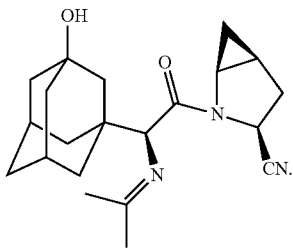

Compound M

12. A crystalline form of Compound M,

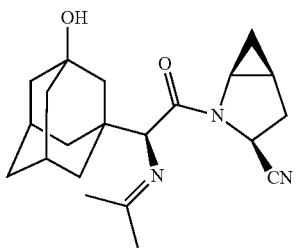

Compound M characterized by data selected from: a powder XRD pattern with peaks at 11.2, 12.6, 14.0, 16.6, and 19.5 ±0.2 degrees 2-theta; a powder XRD pattern substantially as depicted in FIG. 7; a solid state NMR with peaks at 171.43, 42.13 and 29.83 ppm±0.2 ppm; a solid state NMR pattern substantially as depicted in FIG. 13; and combinations thereof.

13. Crystalline compound M according to claim 12, further characterized by data selected from additional powder XRD peaks at 14.5, 19.1 and 30.2±0.2 degrees 2-theta; a FT-IR spectrum substantially as depicted in FIG. 8; a FT Raman spectrum substantially as depicted in FIG. 9; a DSC thermogram substantially as depicted in FIG. 10; and combinations thereof.

14. A process for preparing Saxagliptin, a Saxagliptin salt or a hydrate thereof, said process comprising preparing a Saxagliptin Schiff base as defined in claim 1 and converting it to Saxagliptin, a Saxagliptin salt or a hydrate thereof.

15. The process according to claim 14 wherein the Saxagliptin Schiff base is converted to Saxagliptin, a Saxagliptin salt or a hydrate thereof by hydrolysis.

16. The process according to claim 15 wherein the hydrolysis is carried out by exposure of the Saxagliptin Schiff base to water.

17. The process according to claim 15, wherein the Saxagliptin, Saxagliptin salt or a hydrate thereof is prepared by a process comprising maintaining the Saxagliptin Schiff base, in a relative humidity of about 100%, for a period of about 24 hours.

18. The process according to any of claims 15, wherein the Saxagliptin, Saxagliptin salt or a hydrate thereof is prepared by a process comprising:
  a) suspending the Saxagliptin Schiff base in water; and
  b) optionally recovering Saxagliptin, a Saxagliptin salt or a hydrate thereof.

19. The process according to claim 15, wherein a Saxagliptin salt is prepared by a process comprising:
  a) dissolving the Saxagliptin Schiff base in a suitable solvent;
  b) adding an acid and optionally water; and
  c) recovering the Saxagliptin salt.

20. A process for preparing Saxagliptin, a Saxagliptin salt or a hydrate thereof, said process comprising:
  a. hydrolyzing a compound according to formula Ia:

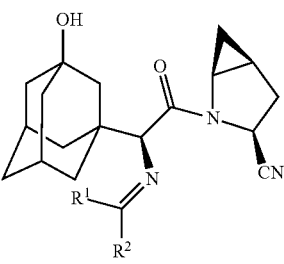

Formula Ia wherein $R^1$ is —H or $C_{1-4}$ alkyl and $R^2$ is —H or $C_{1-4}$ alkyl, phenyl or substituted phenyl; and
  b. recovering Saxagliptin, a Saxagliptin salt or a hydrate thereof.

21. The process according to claim 20, wherein the Formula Ia compound is Compound M:

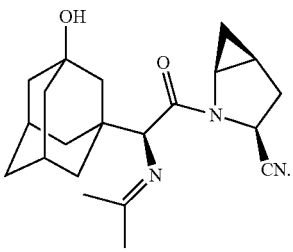

Compound M

22. A process for purifying Saxagliptin comprising preparing a Saxagliptin Schiff base according to Formula I:

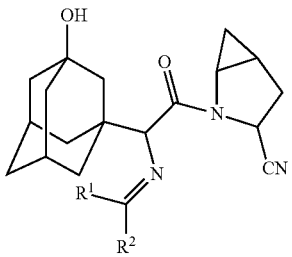

Formula I wherein $R^1$ is —H or $C_{1-4}$ alkyl and $R^2$ is —H or $C_{1-4}$ alkyl, phenyl or substituted phenyl; and converting the compound of formula I to Saxagliptin.

23. A pharmaceutical composition comprising a compound as defined in claim 1, and at least one pharmaceutically acceptable excipient.

24. A method of treating a patient with type 2 diabetes, comprising administering to said patient an effective amount of the pharmaceutical composition according to claim

* * * * *